(12) United States Patent
McKenna et al.

(10) Patent No.: US 8,940,313 B2
(45) Date of Patent: Jan. 27, 2015

(54) TYROSINE-BASED PRODRUGS OF ANTIVIRAL AGENTS

(75) Inventors: Charles E. McKenna, Pacific Palisades, CA (US); Boris A. Kashemirov, Los Angeles, CA (US); Ivan S. Krylov, Los Angeles, CA (US); Michaela Serpi, Cardiff (GB); Valeria M. Zakharova, Los Angeles, CA (US); Larryn W. Peterson, Mountain View, CA (US); John M. Hilfinger, Ann Arbor, MI (US)

(73) Assignee: University of Southern California, Los Angeles, CA (US)

( * ) Notice: Subject to any disclaimer, the term of this patent is extended or adjusted under 35 U.S.C. 154(b) by 34 days.

(21) Appl. No.: 13/092,939

(22) Filed: Apr. 23, 2011

(65) Prior Publication Data

US 2011/0263535 A1 Oct. 27, 2011

Related U.S. Application Data

(60) Provisional application No. 61/327,628, filed on Apr. 23, 2010.

(51) Int. Cl.
| | | |
|---|---|---|
| *A01N 25/34* | (2006.01) | |
| *C07F 9/6561* | (2006.01) | |
| *A61K 31/675* | (2006.01) | |
| *C07F 9/6512* | (2006.01) | |
| *C07F 9/6571* | (2006.01) | |

(52) U.S. Cl.
CPC ........... *C07F 9/65616* (2013.01); *A61K 31/675* (2013.01); *C07F 9/65121* (2013.01); *C07F 9/657181* (2013.01)
USPC ........................................................ 424/402

(58) Field of Classification Search
CPC .... A61K 39/3955; A61K 35/76; A61K 39/42
See application file for complete search history.

(56) References Cited

U.S. PATENT DOCUMENTS

| | | | |
|---|---|---|---|
| 6,037,335 | A | 3/2000 | Takashima et al. |
| 7,193,081 | B2 | 3/2007 | Kopcho et al. |
| 7,214,668 | B2 | 5/2007 | Reddy et al. |
| 7,511,051 | B2 * | 3/2009 | McKenna et al. ............. 514/274 |
| 8,063,209 | B2 | 11/2011 | Hilfinger et al. |
| 2007/0003608 | A1 | 1/2007 | Almond et al. |
| 2009/0270618 | A1 | 10/2009 | Hilfinger et al. |
| 2010/0081628 | A1 | 4/2010 | Du et al. |

OTHER PUBLICATIONS

Vig et al., J. Med. Chem. 2006, 49, 3636-3644 (as cited in the Applicant Arguments/Remarks dated 06/24/20130).*
Analog as defined by National Cancer Institute available via http://www.cancer.gov/dictionary?CdrID=44919.*
Grimm et al., Tetrahedron Letters, 2007, 48, 4509-4513.*
Analog as defined by National Cancer Institute available via http://www.cancer.gov/dictionary?CdrID=44919, downloaded on Feb. 27, 2014.*
PCT Search Report and Written Opinion dated Jan. 19, 2012 and issued in connection with related PCT/US2011/033703.
Clercq, E. D.; Holy, A.; Rosenberg, I.; Sakuma, T.; Balzarini, J.; Maudgal, P. C. A novel selective broad-spectrum anti-DNA virus agent. Nature 1986, 323, 464-467.
Clercq, E. D.; Sakuma, T.; Baba, M.; Pauwels, R.; Balzarini, J.; Rosenberg, I.; Holy, A. Antiviral activity of phosphonylmethoxyalkyl derivatives of purine and pyrimidines. Antiviral Research 1987, 6, 261-272.
Cundy, K. C.; Bidgood, A. M.; Lynch, G.; Shaw, J. P.; Griffin, L., Lee, W. A. Pharmacokinetics, bioavailability, metabolism, and tissue distribution of cidofovir (HPMPC) and cyclic HPMPC in rats. Drug Metabolism and Disposition 1996, 24, 745-752.
Bijsterbosch MK, S. L., van Berkel TJ. Disposition of the acyclic nucleoside phosphonate (S)-9-(3-hydroxy-2-phosphonylmethoxypropyl)adenine. Antimicrob Agents Chemother. 1998 1998, 42, 1146-50.
Cundy KC, L. Z., Hitchcock MJ. Lee WA. Pharmacokinetics of cidofovir in monkeys. Evidence for a prolonged elimination phase representing phosphorylated drug. Drug Metab Dispos. 1996, 24. 738-44.
Peterson, L. W.; McKenna, C. E. Prodrug approaches to improving the oral absorption of antiviral nucleotide analogues. Expert Opinion on Drug Delivery 2009, 6, 405-420.
Eriksson, U.; Peterson, L. W.; Kashemirov, B. A.; Hilfinger, J. M.; Drach, J. C.; Borysko, K. Z.; Breitenbach, J. M.; Kim,.J. S.; Mitchell, S.; Kijek, P.; McKenna, C. E. Serine Peptide Phosphoester Prodrugs of Cyclic Cidofovir: Synthesis, Transport; and Antiviral Activity, Molecular Pharmaceutics 2008, 5, 598-609.
Kikuchi, C.; Nagaso, H.; Hiranuma, T.; Koyama, M. Tetrahydrobenzindoles: Selective Antagonists of the 5-HT7 Receptor. Journal of Medicinal Chemistry 1999; 42, 533-535.
Grimm, J. B.; Wilson, K. J.; Witter, D. J. Suppression of racemization in the carbonylation of amino acid-derived aryl triflates. Tetrahedron Letters 2007, 48, 4509-4513.
Miyazawa T., H. S., Tsuboi Y., Yamada T., Kuwata S. Studies of unusual amino acids and their peptides. XVII. The synthesis of peptides containing N-carboxymethyl amino acids. II. Bull. Chem. Soc. Jpn. 1985, 58, 1976-82.
Cornish, J.; Callon, K. E.; Lin, C. Q. X.; Xiao; C. L.; Mulvey, T. B.; Cooper, G. J. S.; Reid, I. R. Trifluoroacetate, a contaminant in purified proteins, inhibits proliferation of osteoblasts and chondrocytes. Am J Physiol Endocrinol Metab 1999. 277, E779-763.

(Continued)

*Primary Examiner* — Marcela M Cordero Garcia
*Assistant Examiner* — Kaipeen Yang
(74) *Attorney, Agent, or Firm* — Berliner & Associates

(57) ABSTRACT

A tyrosine-based (phosphonylmethoxyalkyl)purine or -pyrimidine conjugate is provided. In some embodiments, the conjugate includes tyrosine based amino acid or dipeptide moieties of (S)-9-(3-hydroxy-2-phosphonyl-methoxypropyl) adenine or its cytosine analog. A method of synthesizing such conjugates based on Boc-protected amino acid or dipeptides is also provided. In addition, a method of isomerizing an (S,S)-diastereoisomer to an (S,R)-diastereoisomer of an amino acid-based or dipeptide-based conjugate by a process including transesterification is provided. A method of inhibiting viral infection and a method of treating viral infection based on (phosphonylmethoxyalkyl)purine or -pyrimidine conjugates is also provided.

17 Claims, 3 Drawing Sheets

(56) References Cited

OTHER PUBLICATIONS

De Clercq E, Neyts, Therapeutic potential of nucleoside/nucleotide analogues against poxvirus infections, J Rev Med Virol. Sep.-Oct. 2004;14(5):289-300.

Turk, S. R.; Shipman, C., Jr.; Nassiri, R.; Genzlinger, G.; Krawczyk, S. H.; Townsend, L. B.; Drach, J. C. Pyrrolo[2,3-d] pyrimidine nucleosides as inhibitors of human cytomegalovirus. Antimicrob. Agents Chemother. 1987, 31, 544-550.

Prichard, M. N,; Turk, S. R.; Coleman, L. A.; Engelhardt, S. L.; Shipman, C., Jr.; Drach, J. C. A microtiter virus yield reduction assay for the evaluation of antiviral compounds against human cytomegalovirus and herpes simplex virus, J. Virol. Methods 1990, 28, 101-106.

Kern, E. R.; Hartline, C.; Harden, E.; Keith, K.; Rodriguez, N.; Beadle, J. R.; Hostetler, K. Y. Enhanced inhibition of orthopoxvirus replication in vitro by alkoxyalkyl esters of cidofovir and cyclic cidofovir. Antimicrob. Agents Chemother, 2002, 46, 991-995.

\* cited by examiner

1 (S)-HPMPA

2 (S)-HPMPC

TYROSINE-BASED PRODRUGS OF ANTIVIRAL AGENTS

CROSS-REFERENCE TO RELATED APPLICATIONS

This application claims the benefit of Provisional Patent Application No. 61/327,628, filed on Apr. 23, 2010, which is incorporated by reference herein.

STATEMENT REGARDING FEDERALLY SPONSORED RESEARCH OR DEVELOPMENT

This invention was made with Government support under Grant Nos. U01 AI061457 and R44 AI056864 from the National Institutes of Health. The Government has certain rights in this invention.

BACKGROUND

1. Field of the Invention

The invention relates to nucleoside phosphonate compounds and methods of synthesis, isomerization and uses thereof.

2. Related Art

Acyclic nucleoside phosphonates (ANPs) are broad spectrum antiviral agents that are highly potent against orthopox viruses, including cowpox, vaccinia, and variola (smallpox) virus. The prototype member of the ANPs is (S)-9-(3hydroxy-2-phosphonyl-methoxypropyl)adenine ((S)-HPMPA, 1) (FIG. 1), first described 1986 for its activity against DNA viruses [1]. Its cytosine analogue, (S)-HPMPC (cidofovir, 2) [2] (FIG. 1) has been shown to have similar therapeutic potential against virtually all DNA viruses as well as other adeno-, papiloma-, polyoma-, and poxvirus infections. Cidofovir has been formally licensed since 1996 in the clinic as Vistide® for the treatment of AIDS patients infected with cytomegalovirus (CMV). The potential use of variola virus (the etiological agent for smallpox) and other orthopox viruses as bioterrorism weapon has stimulated efforts to develop new drugs for the treatment of these pathogenic viruses.

Cidofovir has so far been the only drug approved to be used in an emergency treatment of smallpox outbreak. Although (S)-HPMPC is highly potent in vitro and in animal model infections, it has low oral bioavailability due to the presence of ionized at physiological pH phosphonic acid group. Therefore, (S)-HPMPC and other ANP are effective only when delivered intravenously [3]. This condition limits therapeutic scope of drugs especially under disruptive conditions of a large-scale biowarfare attack or in limited medical facilities of rural areas. Moreover, after intravenous injection drugs of this class tend to accumulate in the kidney leading to severe renal toxicity and it is therefore necessary to increase hydration and co-administer probenecid to prevent nephrotoxicity [4-6]. Thus, there is a pressing need for a new effective orally bioavailable drugs active against orthopox viruses.

SUMMARY

Acyclic nucleoside phosphonates (ANPs) such as (S)-HPMPA or (S)-HPMPC (cidofovir, Vistide®) are broad spectrum antiviral agents that are highly potent against orthopoxviruses, including cowpox, vaccinia, ectromelia (monkeypox) and smallpox (variola virus). However, low oral bioavailability, caused by ionization of a phosphonic acid group at physiological pH, limits therapeutic scope of these drugs. We are currently developing a peptidomimetic prodrug strategy, which implies the coverage of one negative charge in the drug by conversion to its cyclic form and the other via esterification with a tunable, benign promoiety (amino acid or dipeptide). Utilization of tyrosine esters and alkyl amides as a promoiety allowed us to create non toxic cyclic (S)-HPMPA and (S)-HPMPC phosphonate prodrugs with increased chemical and enzymatic stabilities as well as antiviral activities. Esterification of the remaining POH of cyclic nucleoside phosphonates by the promoiety leads to the formation of a new stereocenter at the phosphorus atom, resulting in generation of two diastereoisomers with different stabilities in phosphate buffer (pH 6.5 and 7.4), intestinal homogenate and in vivo.

Several prodrug approaches to improve oral absorption of antiviral nucleoside analogues by incorporating various phosphonate anion masking groups have been developed [7]. The prodrug approach of the inventors implies coverage of one negative charge in the drug by conversion to its cyclic form and the other by installation of a tunable benign promoiety, such as single amino acid, dipeptide, or tripeptide containing the side chain hydroxyl group [8]. As described herein, a variety of tyrosine alkyl- or aryl-amides and esters as promoieties for the generation of cyclic (S)-HPMPA and (S)-HPMPC phosphonate ester prodrugs is provided.

In one aspect, a tyrosine-based conjugate of the formula (I)

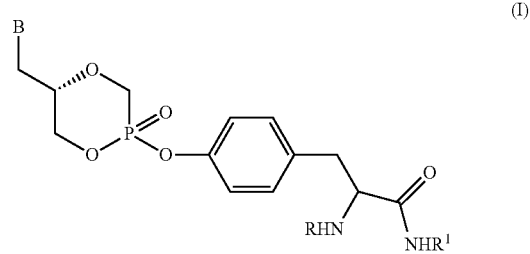

(I)

or a salt thereof is provided, wherein: B is a purine or pyrimidine base, or an analogue thereof; R is H, an amino acid residue or a derivative thereof, or a $C_1$-$C_4$ alkyl, substituted alkyl, cycloalkyl, or substituted cycloalkyl group; and $R^1$ is H or a $C_1$-$C_4$ alkyl, substituted alkyl, cycloalkyl, or substituted cycloalkyl group. In general, "substituted" refers to an alkyl group in which one or more bonds to a hydrogen atom contained within the group are replaced by a bond to a non-hydrogen atom of a substituent group such as hydroxyl, alkoxy, thio, phosphino, amino, halo, silyl, and the like.

In another aspect, a tyrosine-based conjugate of the formula (II)

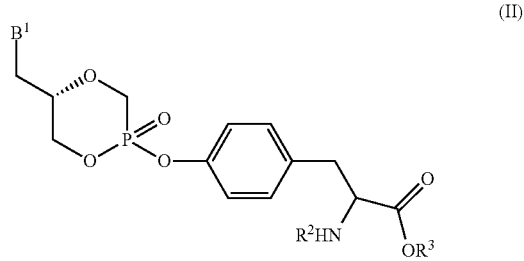

(II)

or a salt thereof is provided, wherein: $B^1$ is a purine or pyrimidine base, or an analogue thereof; $R^2$ is H, an amino acid residue or a derivative thereof, or a $C_1$-$C_4$ alkyl, substituted alkyl, cycloalkyl, or substituted cycloalkyl group; and R³ is H or a C₁-C₄ alkyl, substituted alkyl, cycloalkyl, or substituted cycloalkyl group.

In a further aspect, a tyrosine-based conjugate of the formula (III)

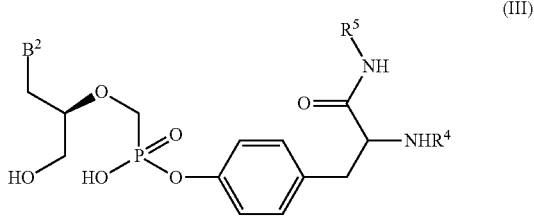

or a salt thereof is provided, wherein: B² is a purine or pyrimidine base, or an analogue thereof; R⁴ is H, an amino acid residue or a derivative thereof, or a C₁-C₄ alkyl, substituted alkyl, cycloalkyl, or substituted cycloalkyl group; and R⁵ is H or a C₁-C₄ alkyl, substituted alkyl, cycloalkyl, or substituted cycloalkyl group.

In some embodiments, Boc-protected conjugates of any compound of formula (I), (II) or (III), or a salt thereof, are provided.

Also provided are pharmaceutical compositions comprising a compound of formula (I), (II) or (III), or a salt thereof, or a combination thereof, and a pharmaceutically acceptable carrier.

In another aspect, a method of inhibiting viral replication in a DNA virus-infected cell is provided. The method includes exposing the cell to a compound of formula (I), (II) or (III), or a salt thereof, or a combination thereof.

In a further aspect, a method of treating a DNA virus infection in an individual is provided. The method includes administering to the individual a therapeutically effective amount of a compound of formula (I), (II) or (III), or a salt thereof, or a combination thereof.

Also provided is a method of synthesizing an amino acid-based conjugate. The method includes coupling a (phosphonylmethoxyalkyl)purine or -pyrimidine to a Boc-protected amino acid, dipeptide, or derivative thereof, in the presence of benzotriazol-1-yl-oxytripyrrolidinophosphonium hexafluorophosphate (PyBOP) as a coupling reagent.

A method of converting an (S,S)-diastereoisomer of an amino acid-based or dipeptide-based conjugate to an (S,R)-diastereoisomer is provided. The method includes transesterifying an (S,S)-diastereoisomer of a Boc-protected amino acid or dipeptide-based (phosphonylmethoxyalkyl)purine or -pyrimidine conjugate.

BRIEF DESCRIPTION OF THE DRAWINGS

For a more complete understanding of the present invention, reference is now made to the following descriptions taken in conjunction with the accompanying drawing, in which.

DETAILED DESCRIPTION

Figure 1:
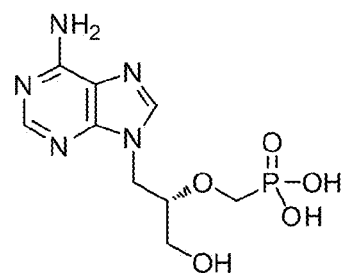
FIG. 1 provides the structures of acyclic nucleoside phosphonates: (S)-HPMPA and (S)-HPMPC.
Figure 1:
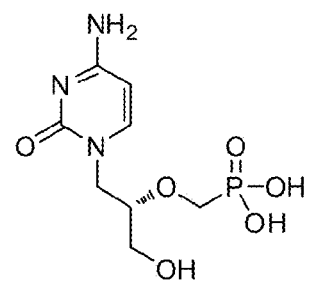

In a compound of formula (I), (II), or (III), or a salt thereof, the group B, B¹, or B², respectively, is a purine or pyrimidine base. The base may be an adenine, guanine, cytosine, uracil or thymine base, including analogues or derivatives thereof with antiviral activity that are known in the art [13]. In some embodiments, the base is an adenine or cytosine base.

In embodiments of the compound of formula (I), (II), or (III), or a salt thereof, the group R, R², or R⁴ may be a valine, alanine, leucine, or isoleucine residue, or derivatives thereof.

The term "amino acid residue" means an amino acid lacking a portion of its structure. Examples include an amino acid without the OH portion of the α-carboxyl group, or lacking the H portion of the α-amino group. Also included within the definition of an amino acid residue is an amino acid lacking a portion of its side chain, such as a serine amino acid lacking the H portion of the side chain —OH group.

A derivative of an amino acid residue is an amino acid residue having a portion of its structure substituted by an atom or molecular group. Examples of such derivatives include, but are not limited to, ester derivatives having an —OR group substituting for the α-carboxyl —OH group, where R is an alkyl or alkenyl group, and amide derivatives having an —NHR group substituting for the α-carboxyl —OH group. In preferred embodiments, R is a C₁-C₄ alkyl or alkenyl group. A dipeptide derivative is a peptide that contains at least one derivative of an amino acid residue.

An amino acid residue may be based on any one of the twenty common amino acids found in naturally synthesized proteins. In some embodiments, the residue provides for oral bioavailability of the compounds described herein. The residue may also be based on a modified or unusual amino acid. Examples of modified or unusual amino acids include, but are not limited to, 2-aminoadipic acid, 3-aminoadipic acid, β-alanine, 2-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, N-methylglycine, N-methylisoleucine, N-methylvaline, norvaline, norleucine, ornithine and homoserine.

Similarly, a dipeptide may contain any of the twenty common amino acids and any of the modified or unusual amino acids. For example, a Boc-protected dipeptide may contain any of the twenty common amino acids.

Both the (D) and (L) stereoisomers of an amino acid residue may be incorporated into the formula (I), (II), or (III) compounds, or salts thereof. When the configuration is not designated, the amino acid or residue can have the configuration (D), (L) or (DL). For the purposes of this application, unless expressly noted to the contrary, a named amino acid shall be construed to include both the (D) or (L) stereoisomers. In some embodiments, the D configuration is selected, while in other embodiments, the L configuration is selected.

In general, the incorporation of one or more amino acids into a (phosphonylmethoxyalkyl)purine or -pyrimidine compound leads to stereoisomeric forms of the compound. The present application contemplates all such forms of the compound, including cis- and trans-isomers, R- and S-enantiomers, diastereomers, (D)-isomers, (L)-isomers, the racemic mixtures thereof, and other mixtures thereof, as falling within the scope of the application. Additional asymmetric carbon atoms may be present in a substituent such as an alkyl group. All such isomers, as well as mixtures thereof, are intended to be included in the application. Some embodiments are individual isomeric forms of the (phosphonylmethoxyalkyl)purine based or -pyrimidine based compounds, which can be isolated for example by high performance liquid chromatography (HPLC).

In embodiments of the compound of formula (I), (II), or (III), or a salt thereof, the group $R^1$, $R^3$, or $R^5$ may be methyl, ethyl, isobutyl, isopropyl, n-propyl, n-butyl, sec-butyl, tert-butyl, or 1,4-dienyl, or derivatives thereof.

In a salt of a compound of formula (I), (II), or (III), the salt may be a pharmaceutically acceptable salt. Pharmaceutically acceptable salts are well known in the art and include salts prepared from pharmaceutically acceptable non-toxic acids, including inorganic acids and organic acids. Suitable non-toxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic acids, and the like. Salts formed with, for example, a free carboxy group of an amino acid residue or a peptide, can be derived from inorganic bases including, but not limited to, sodium, potassium, ammonium, calcium or ferric hydroxides, and organic bases including, but not limited to, isopropylamine, trimethylamine, histidine, and procaine.

In embodiments that include a pharmaceutical composition, the composition may comprise a therapeutically effective amount of a compound of formula (I), (II), or (III), or a salt or pharmaceutically acceptable salt thereof. A therapeutically effective amount of a compound is an amount that results in an improvement or a desired change in condition for which the compound is administered, when the compound is administered once or over a period of time. For example, with respect to virus infections, the improvement can be a lowering of virus titer, or a reduction in the symptoms or discomfort associated with a viral infection. As is known, the amount will vary depending on such particulars as the type of virus infection, the condition being treated, the specific cidofovir compound utilized, the severity of the condition, and the characteristics of the patient.

The pharmaceutical composition will typically contain a pharmaceutically acceptable carrier. Although oral administration is a desired route of administration, other means of administration such as nasal, topical or rectal administration, or by injection or inhalation, are also contemplated. Depending on the intended mode of administration, the pharmaceutical compositions may be in the form of solid, semi-solid or liquid dosage forms, such as, for example, tablets, suppositories, pills, capsules, powders, liquids, suspensions, ointments or lotions, preferably in unit dosage form suitable for single administration of a precise dosage. The compositions may include an effective amount of a selected compound in combination with a pharmaceutically acceptable carrier and, in addition, may include other pharmaceutical agents such as another anti-viral agents, adjuvants, diluents, buffers, and the like. The compound may thus be administered in dosage formulations containing conventional non-toxic pharmaceutically acceptable carriers, adjuvants and vehicles. The amount of active compound administered will be dependent on the subject being treated, the subjects weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions may, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine acetate, triethanolamine oleate, etc. Actual methods of preparing such dosage forms are known, or will be apparent, to those skilled in this art. For oral administration, the composition will generally take the form of a tablet or capsule, or may be an aqueous or nonaqueous solution, suspension or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

In the method of inhibiting viral replication or the method of treating a virus infection, the virus is a DNA virus, which may include, but not limited to, members of the Herpesviridae, Adenoviridae, Polyomaviridae, Poxviridae, Papillomaviridae, Anelloviridae or Parvoviridae families of viruses. Examples of particular viruses include, but are not limited to, cowpox, vaccinia, monkeypox, smallpox, other poxviruses including variola virus and drug-resistant strains thereof, Herpes simplex I, Herpes simplex II, cytomegalovirus, Varicella-Zoster Virus, Epstein-Barr Virus, Human Herpes Virus Type 6, Human Herpes Virus Type 8, Papillomavirus, BK virus and Adenovirus. When inhibiting viral replication or treating a virus infection, a compound of formula (I), (II) or (III), or a salt thereof, or a combination thereof, may be applied or administered. The virus-infected cell may in an individual, may be in an isolated organ, or may be in culture. An individual may be a person or an animal.

In embodiments that include synthesizing an amino acid-based conjugate by a process comprising coupling a (phosphonylmethoxyalkyl)purine or -pyrimidine to a Boc-protected amino acid, dipeptide, or derivative thereof, in the presence of PyBOP, the purine or pyrimidine may be any purine or pyrimidine base included in the formula (I), (II) or (III). Examples of (phosphonylmethoxyalkyl)purine or -pyrimidine compounds include (S)-HPMPA, (S)-HPMPC, and cyclic analogues thereof. The amino acid may be an amino acid or derivative thereof, and the dipeptide may be a dipeptide or derivative thereof. In some embodiments, the Boc-protected amino acid is based on a tyrosine amino acid or dipeptide, such as the Boc-protected amino acid compounds 3a-e, and the Boc-protected dipeptide compound 3f.

In embodiments that include converting an (S,S)-diastereoisomer to an (S,R)-diastereoisomer by a process comprising transesterifying an (S,S)-diastereoisomer of a Boc-protected amino acid or dipeptide-based (phosphonylmethoxyalkyl)

purine or -pyrimidine conjugate, the purine or pyrimidine may be any purine or pyrimidine base included in the formula (I), (II) or (III). The amino acid may be an amino acid or derivative thereof, and the dipeptide may be a dipeptide or derivative thereof. The Boc-protected amino acid-based (phosphonylmethoxyalkyl)purine or -pyrimidine conjugate may be an (S,S)-diastereoisomer of a Boc-protected tyrosine conjugate of any compound of the formula (I), (II) or (III), such as the Boc-protected conjugates Boc-1a, Boc-1e, and Boc-2a-d. The Boc-protected dipeptide-based (phosphonylmethoxyalkyl)purine or -pyrimidine conjugate may be an (S,S)-diastereoisomer of a Boc-protected dipeptide conjugate of any compound of the formula (I), (II) or (III), such as the Boc-protected conjugates Boc-1f and Boc-2f.

The present invention may be better understood by referring to the accompanying examples, which are intended for illustration purposes only and should not in any sense be construed as limiting the scope of the invention.

Example 1

Chemistry

A library of tyrosine (S)-HPMPA and (S)-HPMPC prodrugs has been synthesized as described in Scheme 1. Commercially unavailable NHBoc tyrosine amino acid esters (3b, c) and amides (3d, e) were synthesized according to literature methods [9,10]. Dipeptide 3f was prepared in high yield following a standard coupling procedure using EDC/HOBt in $CH_2Cl_2$ [11]. The coupling reactions between either (S)-HPMPA 1 or (S)-HPMPC 2 with amino acids 3a-e or dipeptide 3f were performed in dimethylformamide (DMF) using diethyisopropylethylamine (DIEA) as the base and benzotriazol-1-yl-oxytripyrrolidinophosphonium hexafluorophosphate (PyBOP) as coupling reagent at 35-40° C. The reaction was monitored by $^{31}$P-NMR and stopped when cHPMPC or cHPMPA, which are firstly formed in the reaction, were no longer present. After solvent removal under reduced pressure, the residue was purified using column chromatography yielding BOC-protected intermediates (Boc-1a,e,f; Boc-2a-d,f) as mixtures of two diastereoisomers, major, (S,S) and minor, (S,R), in a ratio close to 4:1.

Scheme 1

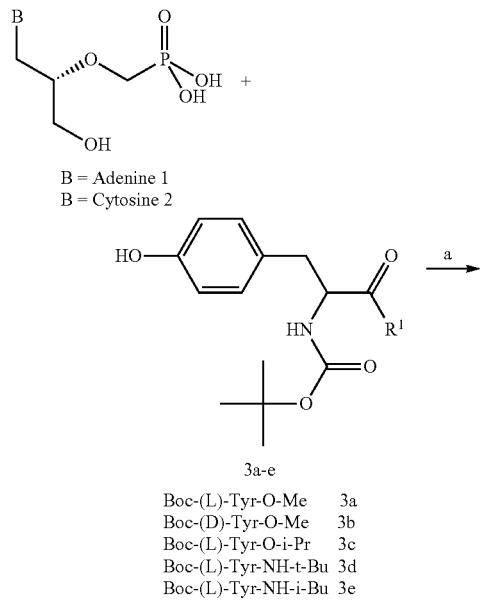

Boc-(L)-Tyr-O-Me 3a
Boc-(D)-Tyr-O-Me 3b
Boc-(L)-Tyr-O-i-Pr 3c
Boc-(L)-Tyr-NH-t-Bu 3d
Boc-(L)-Tyr-NH-i-Bu 3e

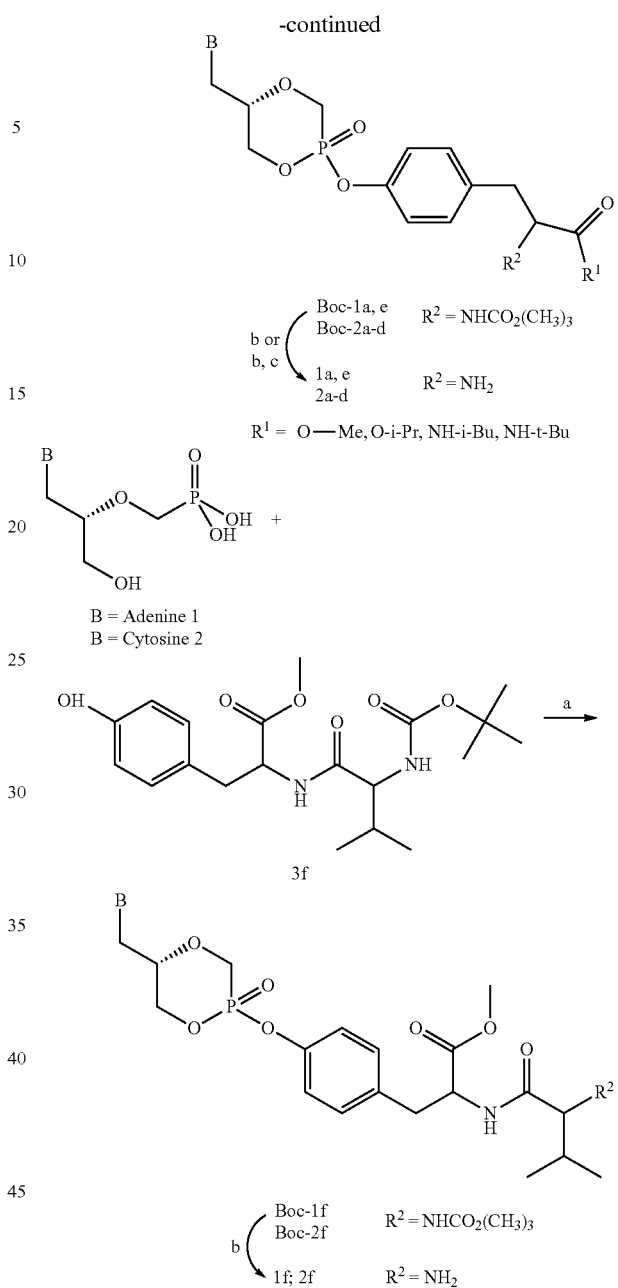

For Scheme 1, synthesis of the amino acid/dipeptide cHPMPC and cHPMPA conjugates 1a,e,f and 2a-d,f, the reagents and conditions are: a) PyBOP, DIEA, DMF, 35-40° C., 2 h; b) TFA, $CH_2Cl_2$, rt; c) 0.1 M HCl/MeOH soln., −20° C.

In the next step, the tert-butoxycarbonyl group was removed using trifluoroacetic acid (TFA) in dichloromethane ($CH_2Cl_2$). The reaction mixture was purified by column chromatography, eluting the product with a mixture of methanol and dichloromethane with addition of a small amount of TFA (0.5%) to prevent decomposition of the prodrug during purification. The prodrugs (1a,e,f; 2a-d,f) were precipitated from methanol by addition of diethyl ether ($Et_2O$). Since any counterion used in pharmaceuticals must be safe and not hamper biological assays, the TFA salts of compounds 1a, e and 2a were converted into their respective hydrochloride salts using 0.1N HCl methanolic solution at −20° (ratio of diastereoisomers did not change). TFA at the concentrations present in commercial peptides has been shown to possess significant biological activity, inhibiting proliferation of osteoblasts and chondrocytes [12].

Isomerization

Esterification of the remaining POH of the cyclic nucleoside phosphonates by the promoiety leads to the formation of a new stereocenter at the phosphorus atom, resulting in generation of two diastereoisomers with different stabilities in phosphate buffer (pH 6.5 and 7.4) and intestinal homogenate. The ratio of diastereoisomers after the coupling reaction is approximately 4:1 with less stable (S,S)-isomer predominating. An approach is developed to convert the (S,S)-diastereoisomer into the more stable (S,R)-one. The major (S,S)-diastereoisomer of Boc-1e or Boc-2c was converted for the most part (around 90%) into (S,R)-diastereoisomer by means of a transesterification process. The reaction was monitored by $^{31}$P NMR. Once completed, the inorganic salt was filtered off, the solvent was removed from the filtrate under reduced pressure, and the residue was directly treated with TFA in dichloromethane affording 1f or 2c, as a diastereoisomeric mixture enriched with the (S,R)-isomer (Scheme 2).

Scheme 2

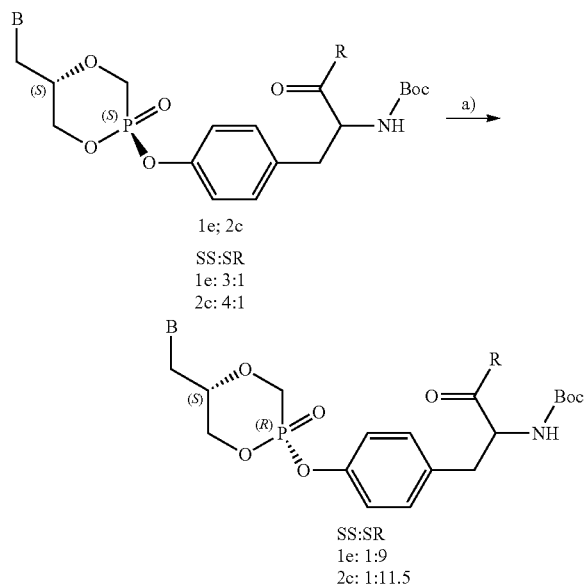

1e; 2c
SS:SR
1e: 3:1
2c: 4:1

SS:SR
1e: 1:9
2c: 1:11.5

For Scheme 2, isomerization, the reagents and conditions are: a) $Cs_2CO_3$, DMF, 0.1 eq. of 3e or 3c respectively.

The absolute configuration of the prodrugs was established by X-ray crystallography performed on model compounds, namely cyclic (S)-HPMPA and (S)-HPMPC phenyl esters. The two diastereoisomers (S,S) and (S,R) of each cyclic nucleoside phosphonate phenyl ester were synthesized according to Scheme 3 and analyzed structurally using X-Ray crystallography.

Scheme 3

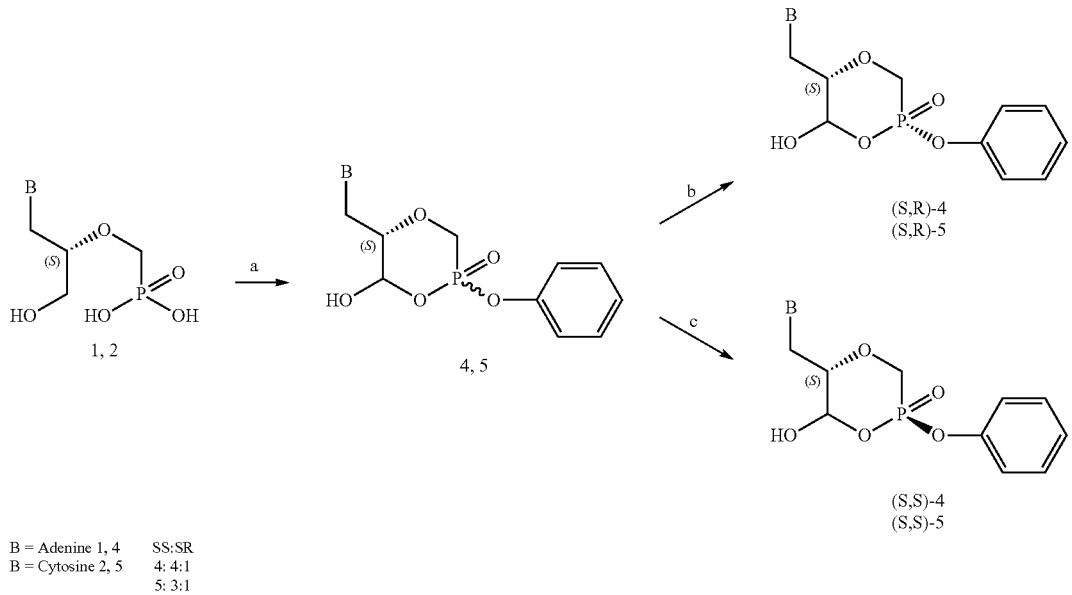

B = Adenine 1, 4    SS:SR
B = Cytosine 2, 5    4: 4:1
                     5: 3:1

(S,R)-4
(S,R)-5

(S,S)-4
(S,S)-5

For Scheme 3, the reagents and conditions are: a) PyBOP, DIEA, DMF, 40° C., 2 h; b) $Cs_2CO_3$, DMF, PhOH; recrystallization from MeOH/acetone (for 4) or $CH_3CN$ (for 5); c) recrystallization from MeOH/acetone/hexane (for 4) or $CH_3CN$ (for 5).

Figure 3A:
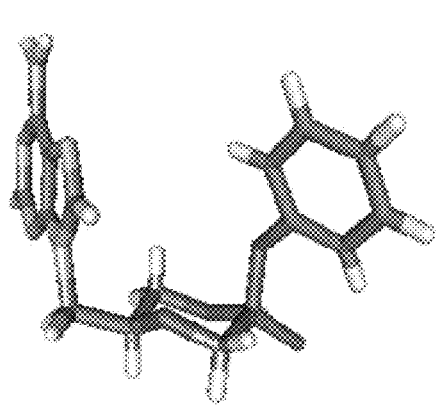
FIG. 3 provides crystal structures of 4-amino-1-{[2-oxo-2-phenoxy-1,4,2λ⁵-dioxaphosphinan-5-yl]methyl}-1,2,3,4-tetrahydropyrimidin-2-one, 4, where (A) is the (2R,5S)-diastereoisomer, and (B) is the (2S,5S)-diastereoisomer.
Figure 3B:
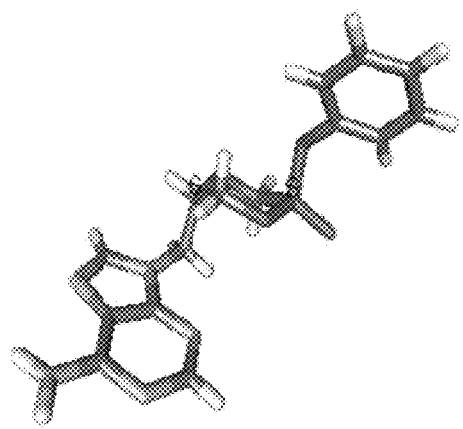
Figure 2:
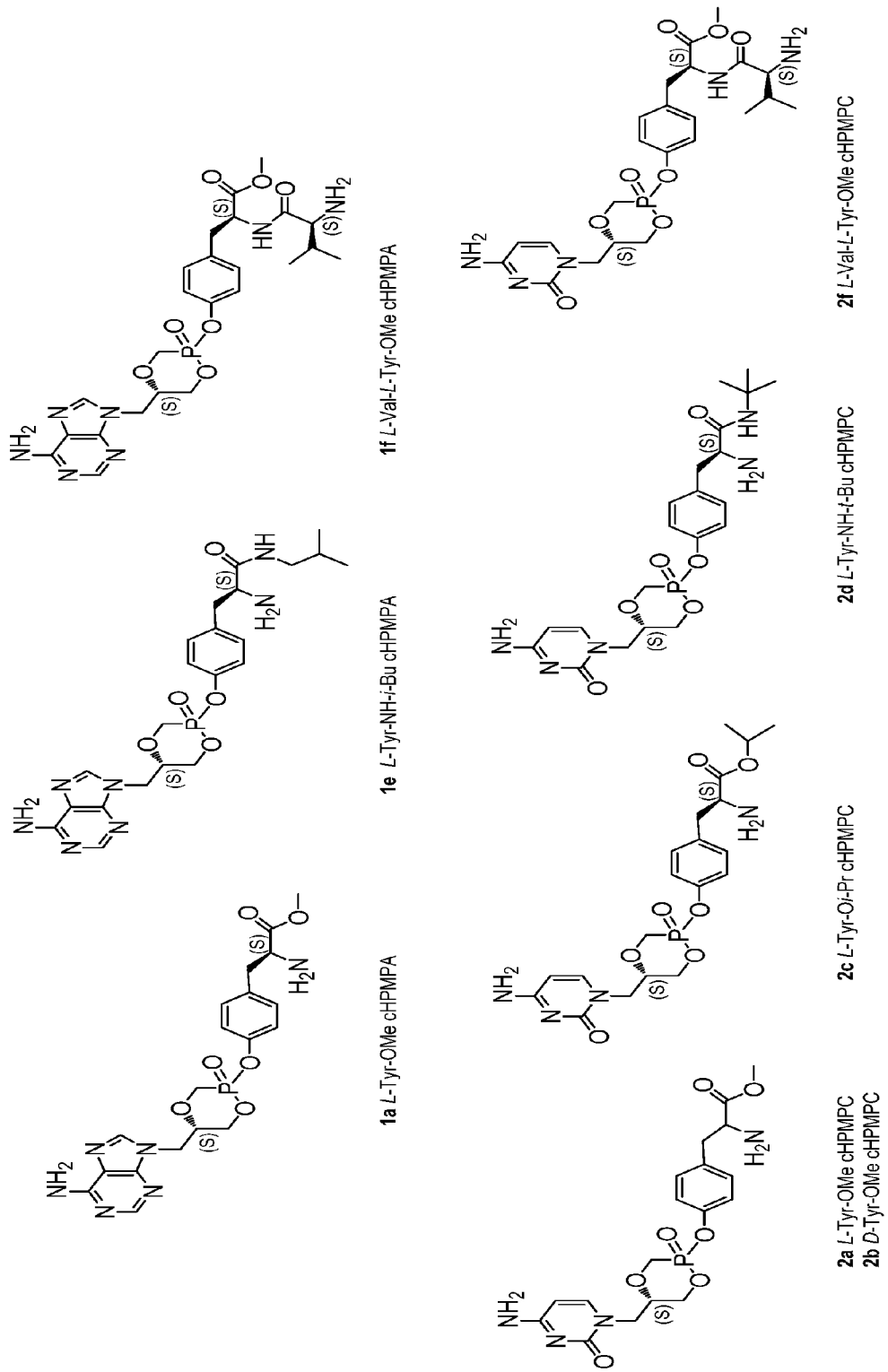
FIG. 2 provides structures of synthesized single amino acid/dipeptide cHPMPC and cHPMPA conjugates 1a,e,f; 2a-d,f.
Figure 4A:
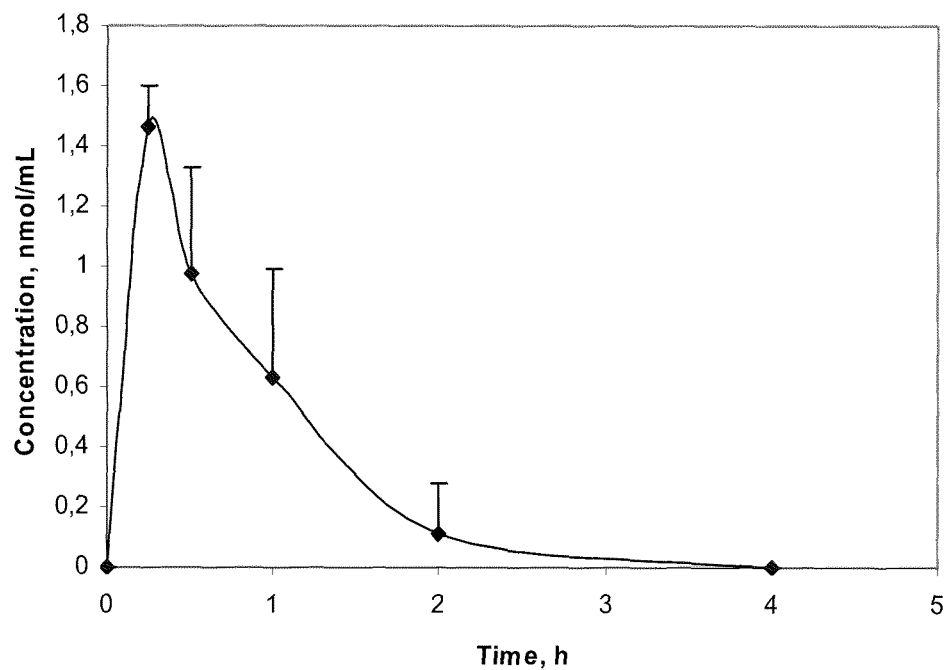
FIG. 4 are graphs showing the plasma levels of total HPMPA-containing species (cHPMPA and prodrug 1e) after intravenous (FIG. 4A) and intestinal dosing (FIG. 4B) of L-Tyr(NH-i-Bu) cHPMPA. Error bars represent standard deviation from five experiments. The AUC values from the curves were used to calculate the bioavailability.
Figure 4B:
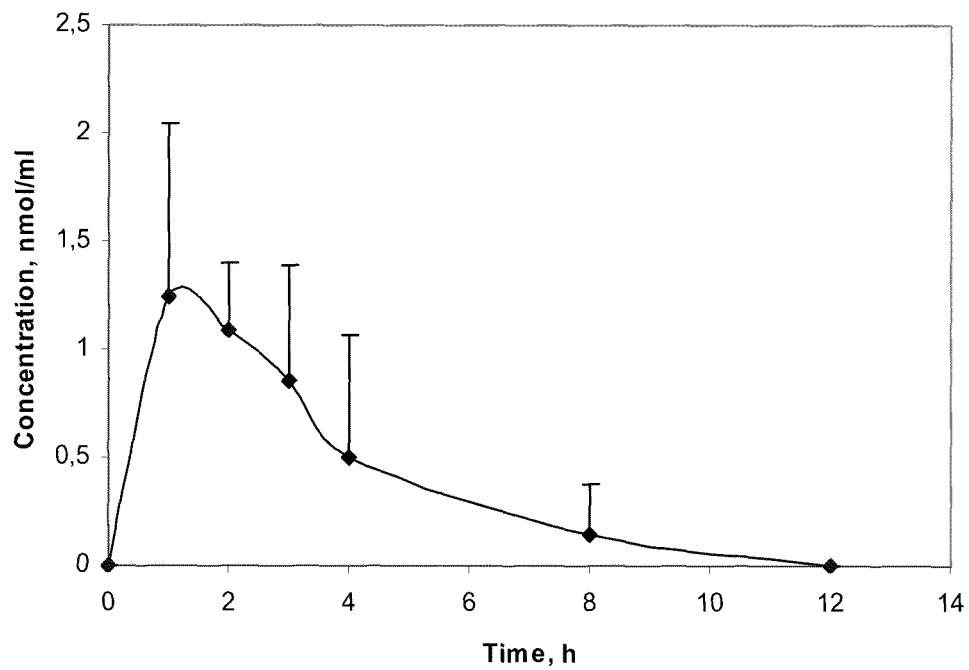

The crystal structures of (S)-HPMPA phenyl esters (S,S)-4, (S,R)-4 revealed that both diastereoisomers crystallized in chair conformations. The OPh-group occupies an axial position in both diastereoisomers, whereas the base changes its position from axial in the (S,S)-4 diastereoisomer to equatorial in the (S,R)-4 diastereoisomer (FIG. 3). The phosphorus atom in the "stable" diastereoisomer is in the R-configuration and corresponds to an upfield signal in the $^{31}$P NMR with respect to the other diastereoisomer. On the other hand, the phosphorus atom in the "unstable" diastereoisomer is in the S-configuration and corresponds to the downfield signal in the $^{31}$P NMR (FIG. 3B).

Stability and Hydrolysis Studies

In order to increase oral bioavailability and intracellular delivery, an ideal oral prodrug must survive the gastrointestinal (GI) tract, be absorbed across intestinal mucosa and delivered into the systemic circulation following its active/passive transport, and then be distributed into cells where has to be converted to the parent drug. Therefore, stability is one of the major factors influencing the design of ANP prodrugs. Chemical and enzymatic stabilities of the novel prodrugs (1a,e,f; 2a-d,f) were studied using LC-MS analysis. The chemical stability was determined by evaluating the hydrolysis rates of the prodrugs in 200 mM phosphate buffer at physiologically relevant pH (6.5 and 7.4) and temperature (37° C.). To assess the enzymatic stability, the rate of hydrolysis of each prodrug was determined in rat intestinal homogenate (Int. Hom.) with pH 6.5 at 37° C. The chemical and enzymatic hydrolysis of each prodrug followed pseudo-first-order kinetics over several half-lives ($t_{1/2}$). Half-lives of the tyrosine prodrugs are reported in Table 1. The tyrosine cHPMPA and cHPMPC prodrugs proved to be chemically stable with a significant difference between the two diastereoisomers. On the other hand, a large reduction in the half-lives is observed in intestinal homogenate compared to buffer solutions. This drop in stability is largely avoided if a (D)-amino acid (2b) or N-alkyl amide amino acids (1e, 2d) are used.

Table 1 provides the experimentally determined half-lives of the cHPMPC and cHPMPA prodrugs in phosphate buffer with pH 6.5 and 7.4 and in cell tissue homogenates, pH 6.5 at 37° C.

TABLE 1

| Compound | Isomer | $T_{1/2}$ (min) Buffer pH 6.5 | pH 7.4 | Int. Hom. |
|---|---|---|---|---|
| L-Tyr-O-Me cHPMPC (2a) | (S,R) | 247 | 121 | <30 |
|  | (S,S) | 56 | 19 | <30 |
| D-Tyr-O-Me cHPMPC (2b) | (S,R) | 407 | 126 | 210 |
|  | (S,S) | 95 | 21 | 72 |
| L-Tyr-O-i-Pr cHPMPC (2c) | (S,R) | 770 | 239 | <30 |
|  | (S,S) | 121 | 22 | <30 |
| D-Tyr-NH-t-Bu cHPMPC (2d) | (S,R) | 1732 | 630 | 1732 |
|  | (S,S) | 182 | 60 | 203 |
| L-Tyr-O-Me cHPMPA (1a) | (S,R) | 330 | nd | <28 |
|  | (S,S) | 55 | nd | <28 |
| L-Tyr-NH-i-Bu cHPMPA (1e) | (S,R) | 990 | 277 | 630 |
|  | (S,S) | 122 | 26 | 114 |
| L-Val-(L)-Tyr-O-Me cHPMPA (1f) | (S,R) | 346 | 61 | <28 |
|  | (S,S) | 67 | 12 | <28 |
| L-Val-(L)-Tyr-O-Me cHPMPC (2f) | (S,R) | 346 | 66 | <28 |
|  | (S,S) | 95 | 15 | <28 |
| L-Tyr-NH-i-Bu HPMPA (8) |  | st | st | st |

*a* st = stable and nd = not determined

LC-MS analysis of the chemical and enzymatic hydrolysis of tyrosine linked dipeptide cHPMPC and cHPMPA conjugates 1f and 2f identified several metabolic and hydrolysis pathways: 1) cyclization of the dipeptide promoiety to form a diketopiperazine ring (DKP), 2) opening of the endocyclic PO bond, 3) hydrolysis of the ester group 4) hydrolysis of the promoiety with direct release of the parent drug (12-20%). On the other hand, chemical hydrolysis of single amino acids conjugates 1a and 2a-c in phosphate buffer (pH 6.5 and 7.4) resulted in formation of two main products: cyclic HPMPA (or HPMPC) and acyclic tyrosine HPMPA (or HPMPC) conjugate. To avoid further premature removal of the amino acid ester group and generation of additional metabolites, the corresponding N-alkyl amides 1e and 2d were therefore synthesized.

Only two products, namely cyclic phosphonate (cHPMPA, 6 or cHPMPC, 7) and acyclic phosphonate tyrosine monoester (L-Tyr-NH-i-Bu cHPMPA, 1e or L-Tyr-NH-t-Bu cHPMPC, 2d) have been observed during metabolism in intestinal homogenate and in plasma. cHPMPA (cHPMPC) was released with 45-50% yield (Scheme 4).

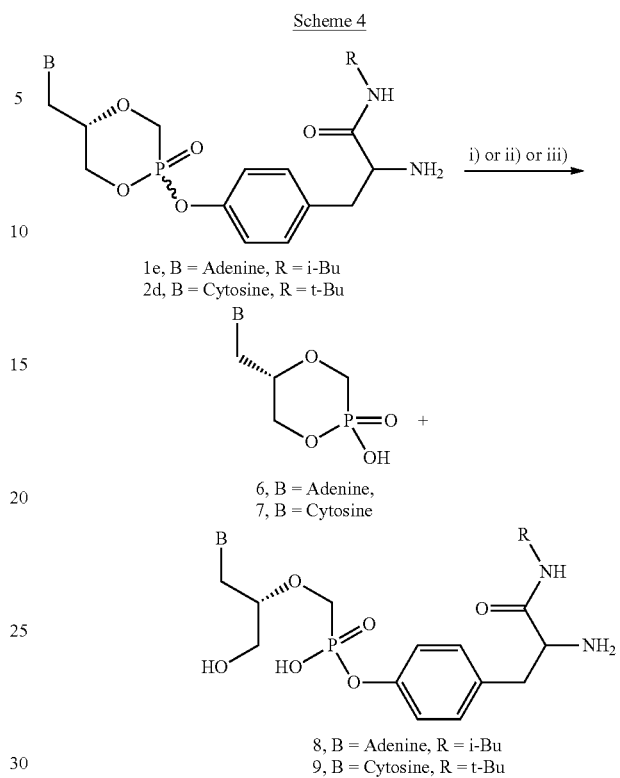

Scheme 4

1e, B = Adenine, R = i-Bu
2d, B = Cytosine, R = t-Bu

6, B = Adenine,
7, B = Cytosine

8, B = Adenine, R = i-Bu
9, B = Cytosine, R = t-Bu

Scheme 4 shows the metabolism pathways observed for tyrosine cHPMPA and cHPMPC conjugates 1e, 2d.in: i) phosphate buffer with pH 6.5 or 7.4, 37° C.; ii) intestinal homogenate, pH 6.5, 37° C.; iii) rat plasma, pH 7.4, 37° C.

To evaluate the antiviral potential of the second metabolite, acyclic (S)-HPMPA phosphonate tyrosine monoester 8 was purified after hydrolysis of 1e in aq. NH$_4$OH.

Antiviral Activity

The newly synthesized prodrugs, as well as the parent compounds HPMPA and HPMPC, were evaluated for in vitro antiviral activity against various DNA viruses including herpes simplex 1 (HSV-1), human cytomegalovirus (HCMV), and two poxviruses (vaccinia and cowpox viruses).

Propagation of Cells and Virus.

The routine growth and passage of KB cells were performed in monolayer cultures using minimal essential medium (MEM) with either Hanks salts [MEM(H)] or Earle salts [MEM(E)] supplemented with 5% fetal bovine serum. Cells were routinely enumerated with a Coulter Counter model ZF equipped with 100 mm orifice. KB cells were plated at 1×10$^5$ cells/well using 24-well cluster dishes. The routine growth and passage of primary human foreskin fibroblast (HFF) cells and methods for propagation and titration of virus have been previously described by Turk et al. [14]. Viral pools were prepared in HFF cells and were diluted to provide working stocks. All viruses were titered using monolayer cultures of HFF cells [15]. Following incubation for three days (HSV-1 and poxviruses) or 10-12 days (HCMV), cells were fixed and stained with 0.1% crystal violet in 20% methanol and macroscopic plaques (herpes simplex and poxviruses) or microscopic plaques (HCMV) enumerated.

Assays for Antiviral Activity

The effect of compounds on the replication of poxviruses and HCMV was measured using plaque reduction assays [14, 16]. For poxviruses, virus used was diluted in MEM containing 10% FBS to a desired concentration which gave ~50 plaques per well in 6-well cluster plates. Medium then was aspirated from the wells, and 0.2 ml of virus was added to each well in triplicate, with 0.2 ml of medium being added to drug toxicity wells. Plates were incubated for 1 hour with occasional shaking. After the incubation period, an equal amount of 1% agarose was added to an equal volume of each drug dilution. This gave final drug concentrations beginning with 100 µM and ending with 0.03 µM in a methocel overlay. The drug-methocel mixture was added to each well in 2-ml volumes, and the plates were incubated for 3 days, after which cells were stained with 0.1% crystal violet in 20% methanol. After approximately 1 hour, the stain was aspirated and the plaques were counted using a stereomicroscope at ×10 magnification. Similar techniques were used for HCMV differing in that ~100 plaques were used per well in 24-well cluster plates and incubation was for approximately 10 days. Drug effects were calculated as a percentage of the reduction in plaque number in the presence of each drug concentration compared to the numbers obtained in the absence of drug. Cidofovir (CDV) was used as a positive control in all experiments with poxviruses, ganciclovir (GCV) was used as the positive control in all experiments with HCMV. Acyclovir (ACV) was used as a control for experiments with HSV-1.

Dose-response relationships were constructed by linearly regressing the percent inhibition (or corresponding probit values) of plaque reduction against log drug concentrations. The 50% inhibitory ($IC_{50}$) concentrations and corresponding 95% confidence intervals were calculated from the regression lines [17]. Samples containing positive controls were used in all assays. Results from sets of assays were rejected if inhibition by the positive control deviates from its mean response by more than 1.5 standard deviations.

Cytotoxicity Assays.

Effects of all compounds on HFF cells used in plaque reduction assays were scored visually for cytotoxicity. Cytotoxicity to KB cell growth was tested using a colorimetric assay. In HFF cells, cytopathology was estimated at 20- to 60-fold magnification in areas of the assay plate not affected with virus infection and scored on a zero to four plus basis. Cells were scored on the day of staining. In KB cells, the effect of compounds during two population doublings of KB cells was determined by crystal violet staining and spectrophotometric quantization of dye eluted from stained cells as described earlier [15]. Briefly, 96-well cluster dishes were plated with KB cells at 5000 cells per well. After overnight incubation at 37° C., test compound was added in triplicate at eight concentrations. Plates were incubated at 37° C. for 48 h in a $CO_2$ incubator, rinsed, fixed with 95% ethanol, and stained with 0.1% crystal violet. Acidified ethanol was added and plates read at 570 nm in a spectrophotometer designed to read 96-well ELISA assay plates. Dose-response relationships were constructed by linearly regressing the percent inhibition of parameters derived in the preceding sections against log drug concentrations. The 50% inhibitory concentrations were calculated from the regression lines using the methods described by Goldstein [17].

Results of anti-viral activity are provided in Tables 2 and 3.

TABLE 2

Antiviral activity and cytotoxicity of the cHPMPC and cHPMPA prodrugs

| Compounds | $IC_{50}$ (µM) | | | | | |
|---|---|---|---|---|---|---|
| | Cow Pox | Vaccinia | HSV-1 | HCMV | KB | HFF |
| L-Tyr-O-Me cHPMPC (2a)[b] | 50 | 4 | 25 | 0.23 | >100 | >100 |
| D-Tyr-O-Me cHPMPC (2b)[a] | 35 | 25 | 35 | 0.2 | >100 | >100 |
| L-Tyr-O-i-Pr cHPMPC (2c)[a] | 40 | 30 | 20 | 0.12 | >100 | >100 |
| L-Val-L-Tyr-O-Me cHPMPC (2f)[a] | 30 | 20 | 15 | <0.1 | >100 | >100 |
| L-Tyr-O-Me cHPMPA (1a)[b] | 3.5 | 3 | 35 | 0.45 | >100 | >100 |
| L-Val-(L)-Tyr-OMe cHPMPA (1f)[a] | 8 | 4 | 35 | 0.3 | >100 | 100 |
| L-Tyr-NH-i-Bu cHPMPA (1e)[a] | 7 | 4.5 | 50 | 0.3 | >100 | >100 |
| (S)-HPMPC (2) | 30 | 20 | nd | 0.28 | >100 | 100 |
| ACV | nd | nd | 0.6 | nd | nd | nd |
| CDV | 15 | 20 | nd | nd | nd | nd |
| 3L | Nd | nd | nd | nd | 3 | nd | nd = not determined.
[a]trifluoroacetic salt;
[b]hydrochloric salt.

TABLE 3

Antiviral activity and cytotoxicity of the cHPMPA prodrugs

| Compounds | $IC_{50}$ (µM) | | | | | |
|---|---|---|---|---|---|---|
| | Cow Pox | Vaccinia | HSV-1 | HCMV | KB | HFF |
| L-Tyr-NH-i-Bu HPMPA (8)[b] | 3 | 0.5 | 45 | 0.29 | >100 | >100 |
| L-Tyr-NH-i-Bu cHPMPA ((S,R)-1e)[a] | 2.5 | 1 | 100 | 0.55 | >100 | 100 |
| L-Tyr-NH-i-Bu cHPMPA ((S,S)-1e)[a] | 2 | 1.5 | 35 | 1.3 | >100 | >100 |
| (S)-HPMPA (1) | 4 | 2 | 35 | 0.41 | >100 | 100 |
| cHPMPA (6) | 0.6 | 1 | 30 | 1.3 | >100 | 100 |
| ACV | nd | nd | 0.7 | nd | Nd | nd |
| CDV | 20 | 15 | nd | nd | 3 | nd |
| DHPG | nd | Nd | nd | 2.4 | nd | >100 |
| 3L | nd | Nd | nd | nd | 2 | nd | nd = not determined.
[a]trifluoroacetic salt;
[b]acetate salt.

All the tyrosine cHPMPA and cHPMPC prodrugs demonstrated activity against poxviruses with $IC_{50}$ values in a range of 2-50 µM. The stable acyclic metabolite, L-Tyr-NH-i-Bu HPMPA 8 was active against all these viruses as well. The counterion (TFA or chloride) had no significant effect on the antiviral activity of the prodrugs. None of the compounds showed significant cytotoxicity toward stationary or growing cells up to a concentration of 100 µM.

Transport Studies of Tyr(NH-i-Bu) cHPMPA (1e)

Studies on the activation mechanism of Tyr(NH-i-Bu) cHPMPA (1e) (Scheme 5) revealed that, beside the release of the drug (6), as stable metabolite the open form of the prodrug (8) is generated through the endocyclic PO bond cleavage.

Scheme 5

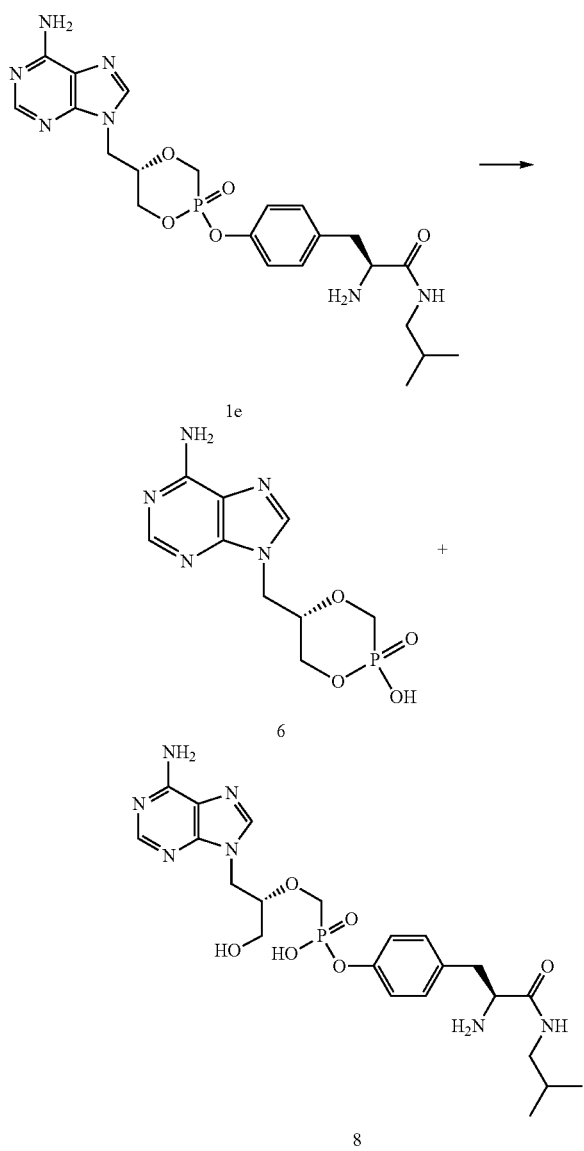

Scheme 5 provides the metabolism pathway observed for Tyr(NH-i-Bu) cHPMPA (1e).

Compound 1e (as the diastereoisomeric mixture) was evaluated for oral bioavailability by direct injection of the drug into the gastrointestinal tract of the mice at a level of 10 mg/kg and comparison of the data obtained with the results for intravenous injection (at a level of 1 mg/kg). Plasma samples obtained from mice were analyzed by LC-MS as described in the experimental part for content of the prodrug 1e and its metabolites 6 and 8. No open prodrug 8 was detected in analyzed samples. Total concentration of HPMPA-containing compounds was calculated as an average of 5 experiments in nmol/mL based on the amounts of prodrug 1e and cHPMPA (6).

The oral uptake of the prodrug was significantly enhanced over the parent compound. Oral bioavailability was calculated from the ratio oral AUC divided by the intravenous AUC data with an adjustment for the differences in the intravenous dose vs oral dose (6 mg oral vs 0.6 mg intravenous). The total bioavailability derived from the oral administration of 1e in this experiment is estimated to be 39% compared to 5% for the parent HPMPA.

Example 2

Experimental

Synthesis of Boc-protected amino acid/dipeptide HPMPC and HPMPA conjugates Boc-1a,e,f and Boc-2a-d,f. General Procedure. To a suspension of HPMPA (1) or HPMPC (2) (1 mmol) in dry DMF (5 mL), dry DIEA (10 mmol, 1.8 mL) was added. The reaction flask was warmed by a heat gun to facilitate the dissolution of the HPMPC/HPMPA-DIEA salt. The volatiles were then removed under vacuum. To the residue anhydrous DMF (5 mL), dry DIEA (10 mmol, 1.8 mL), the relevant amino acid 3a-e or dipeptide 3f (1.5 mmol), and PyBOP (2 mmol, 1.041 g) were added. The reaction mixture was stirred under $N_2$ at 40° C. for 2 h. The reaction was monitored by $^{31}P$ NMR, and additional portions of PyBOP were added as necessary. After reaction completion DMF and DIEA were removed under vacuum. The residue was extracted with diethyl ether and purified by silica gel column chromatography [$CH_2Cl_2$, $CH_2Cl_2$:acetone (2:1), and $CH_2Cl_2$:acetone:$CH_3OH$ (6:3:1)]. Solvents were removed under vacuum to furnish N-Boc protected compounds Boc-1a,e,f and Boc-2a-d,f. In text below (S,S)-diastereoisomer is denoted as A diastereoisomer whereas (S,R)-diastereoisomer is denoted as B.

Methyl-(2)-3-(4-{[(5S)-5-[(4-amino-2-oxo-2H-pyrimidin-1-yl)methyl]-2-oxo-1,4,2$\lambda^5$-dioxaphosphinan-2-yl]oxy}phenyl)-2-{[(tert-butoxy)carbonyl]amino}propanoate (Boc-2a). Yield 57%. Obtained from 1000 mg of HPMPC as mixture of diastereoisomers A:B in ratio 4:1 (by $^{31}P$ NMR). $^1H$-NMR (500 MHz, $CD_3OD$) δ: 7.53 (d, J=7.0 Hz, 1H, CH=CH—N, isomer A), 7.52 (d, J=6.0 Hz, 1H, CH=CH—N, isomer B), 7.21-7.09 (m, 4H, aromatics), 5.85 (d, J=7.5 Hz, 1H, CH=CH—N), 4.59 (ddd, $J_{gem}$=14.5 Hz, J=13.5 Hz, J=2.5 Hz, 1H, isomer A), 4.50-4.26 (m, 3H), 4.15-4.12 (m, 2H), 4.05-3.92 (m, 2H), 3:75 (dd, $J_{gem}$=14.5 Hz, J=7.0 Hz, 1H, $CH_aH_bN$, isomer B), 3.65 (s, 3H, $OCH_3$), 3.06 (dd, $J_{gem}$=14.0 Hz, J=4.5 Hz, 1H, $CH_aH_b$(Tyr)), 2.86 (dd, $J_{gem}$=13.0 Hz, J=9.0 Hz, 1H, $CH_aH_b$(Tyr)), 1.33 (s, 9H, $C(CH_3)_3$). $^{31}P$ NMR (202.5 MHz, $CD_3OD$) δ: 10.10 (isomer A), 8.91 (isomer B).

Methyl-(2R)-3-(4-{[(5S)-5-[(4-amino-2-oxo-2H-pyrimidin-1-yl)methyl]-2-oxo-1,4,2$\lambda^5$-dioxaphosphinan-2-yl]oxy}phenyl)-2-{[(tert-butoxy)carbonyl]amino}propanoate (Boc-2b). Yield 47%. Obtained from 108 mg of HPMPC as a mixture of diastereoisomers A:B in ratio 3.8:1 (by $^{31}P$ NMR). $^1H$ NMR (400 MHz, $CD_3OD$) δ: 7.63-7.60 (m, 1H, CH=CH—N), 7.28-7.5 (m, 4H, aromatics), 5.82-5.89 (m, 1H, CH=CH—N), 4.66 (ddd, $J_{gem}$=14.4 Hz, J=12.4 Hz, J=2.8 Hz, 1H, isomer A), 4.56-3.99 (m, 3H), 4.23-4.18 (m, 2H), 4.09-3.99 (m, 2H), 3.80 (dd, $J_{gem}$=14.4 Hz, J=7.6 Hz, 1H, $CH_aH_bN$, isomer B), 3.72 (s, 3H, $OCH_3$), 3.13 (dd, $J_{gem}$=14.0 Hz, J=5.6 Hz, 1H, $CH_aH_b$(Tyr)), 2.92 (dd, $J_{gem}$=13.6 Hz, J=9.2 Hz, 1H, $CH_aH_b$(Tyr)), 1.40 (s, 9H, $C(CH_3)_3$). $^{31}P$ NMR (162 MHz, $CD_3OD$) δ: 10.02 (isomer A), 8.83 (isomer B).

Propan-2-yl-(2S)-3-(4-{[(5S)-5-[(4-amino-2-oxo-2H-pyrimidin-1-yl)methyl]-2-oxo-1,4,2$\lambda^5$-dioxaphosphinan-2-yl]oxy}phenyl)-2-{[(tert-butoxy)carbonyl]amino}propanoate (Boc-2c). Yield 35%. Obtained from 118 mg of HPMPC as a mixture of diastereoisomers A:B in ratio 3.4:1 (by $^{31}P$ NMR). $^1H$ NMR (400 MHz, $CD_3OD$) δ: 7.61 (d, J=7.6 Hz, 1H, CH=CH—N, isomer A), 7.59 (d, J=7.6 Hz, 1H, CH=CH—

N, isomer B), 7.31-7.15 (m, 4H, aromatics), 5.91 (d, J=7.6 Hz, 1H, CH=CH—N), 5.00-4.95 (m, 1H, OCH(CH$_3$)$_2$), 4.65 (ddd, J$_{gem}$=14.8 Hz, J=12.0 Hz, J=2.4 Hz, 1H, isomer A), 4.69-4.42 (m, 3H), 4.38-4.18 (m, 3H), 4.12-3.96 (m, 2H), 3.81 (dd, J$_{gem}$=14.0 Hz, J=7.2 Hz, 1H, CH$_a$H$_b$N, isomer B), 3.10 (dd, J$_{gem}$=14.0 Hz, J=6.0 Hz, 1H, CH$_a$H$_b$(Tyr)), 2.92 (dd, J$_{gem}$=14.0 Hz, J=9.2 Hz, 1H, CH$_a$H$_b$(Tyr)), 1.41 (s, 9H, C(CH$_3$)$_3$), 1.26 (d, J=6.0 Hz, 3H, CHCH$_3$), 1.19 (d, J=6.4 Hz, 3H, CHCH$_3$). $^{31}$P NMR (162 MHz, CD$_3$OD) δ: 9.98 (isomer A), 8.82 (isomer B).

tert-Butyl-N-[(1R)-2-(4-{[(5S)-5-[(4-amino-2-oxo-2H-pyrimidin-1-yl)methyl]-2-oxo-1,4,2λ$^5$-dioxaphosphinan-2-yl]oxy}phenyl)-1-(tert-butylcarbamoyl)ethyl]carbamate (Boc-2d). Yield 27%. Obtained from 117 mg of HPMPC as a mixture of diastereoisomers A:B in ratio 1.8:1 (by $^{31}$P NMR). $^1$H NMR (400 MHz, CD$_3$OD) δ: 7.58 (d, J=6.8 Hz, 1H, CH=CH—N, isomer A), 7.59 (d, J=7.6. Hz, 1H, CH=CH—N, isomer B), 7.31-7.14 (m, 4H, aromatics), 5.89 (d, J=7.2 Hz, 1H, CH=CH—N, isomer B), 5.88 (d, J=7.6 Hz, 1H, CH=CH—N, isomer A), 4.65 (ddd, J$_{gem}$=14.8 Hz, J=12.0 Hz, J=2.4 Hz, 1H, isomer A), 4.58-4.41 (m, 2H), 4.33 (dd, J$_{gem}$=14.8 Hz, J=10.8 Hz, 1H, isomer B), 4.25-4.17 (m, 3H), 4.12-4.02 (m, 1H), 3.96 (dd, J$_{gem}$=14.4 Hz, J=8.0 Hz, 1H), 3.82 (dd, J$_{gem}$=14.4 Hz, J=7.2 Hz, 1H, CH$_a$H$_b$N, isomer B), 3.02-2.97 (m, 1H, CH$_a$H$_b$ (Tyr)), 2.87-2.81 (m, 1H, CH$_a$H$_b$ (Tyr)), 1.41 (s, 9H, C(CH$_3$)$_3$, isomer B), 1.40 (s, 9H, C(CH$_3$)$_3$, isomer A), 1.29 (s, 9H, NH(CH$_3$)$_3$). $^{31}$P NMR (162 MHz, CD$_3$OD) δ: 9.92 (isomer A), 8.68 (isomer B).

Methyl(2S)-3-(4-{[(5S)-5-[(6-amino-9H-purin-9-yl)methyl]-2-oxo-1,4,2λ$^5$-dioxaphosphinan-2-yl]oxy}phenyl)-2-{[(tert-butoxy)carbonyl]amino}propanoate (Boc-1a). Yield 73%. Obtained from 750 mg of HPMPA as mixture of diastereoisomers A:B in ratio 4:1 (by $^{31}$P NMR). $^1$H NMR (400 MHz, CD$_3$OD) δ: 8.25 (s, 1H, 2-H), 8.17 (s, 1H, 8-H, isomer A), 8.15 (s, 1H, 8-H, isomer B), 7.28-7.04 (m, 4H, aromatics), 4.76-4.07 (m, 7H), 3.73 (s, 3H, OCH$_3$, isomer B), 3.72 (s, 3H, OCH$_3$, isomer A), 3.15 (dd, J$_{gem}$=14.0 Hz, J=5.3 Hz, 1H, CH$_a$H$_b$(Tyr)), 2.91 (dd, J$_{gem}$=14.0 Hz, J=9.2 Hz, 1H, CH$_a$H$_b$ (Tyr)), 1.41 (s, 9H, C(CH$_3$)$_3$, isomer B), 1.39 (s, 9H, C(CH$_3$)$_3$, isomer A). $^{31}$P NMR (162 MHz, CD$_3$OD) δ: 9.84 (isomer A), 8.61 (isomer B).

iso-Butyl N-[2-(4-{[(5S)-5-[(6-amino-9H-purin-9-yl)methyl]-2-oxo-1,4,2λ$^5$-dioxaphosphinan-2-yl]oxy}phenyl)-1-[(2-methylpropyl)carbamoyl]ethyl]carbamate (Boc-1e). Yield 76%. Obtained from 1000 mg of HPMPA as mixture of diastereoisomers A:B in ratio 4.4:1 (by $^{31}$P NMR). $^1$H NMR (400 MHz, CD$_3$OD): δ 8.26 (s, 1H, 2-H, isomer B), 8.25 (s, 1H, 2-H, isomer A), 8.17 (s, 1H, 8-H, isomer A), 8.14 (s, 1H, 8-H, isomer B), 7.30 (d, J=8.6 Hz, 2H, aromatics, isomer A), 7.15 (d, J=8.0 Hz, 2H, aromatics, isomer A), 7.11 (d, J=8.6 Hz, 2H, aromatics, isomer B), 6.76 (d, J=8.0 Hz, 2H, aromatics, isomer B), 4.78-4.06 (m, 8H), 3.09-2.81 (m, 4H), 1.72 (m, J=6.7 Hz, CH(CH$_3$)$_2$), 1.41 (s, 9H, C(CH$_3$)$_3$, isomer B), 1.39 (s, 9H, C(CH$_3$)$_3$, isomer A), 0.86 (m, 6H, 2CH$_3$). $^{31}$P NMR (202.5 MHz, CD$_3$OD): 11.43 (isomer A), 10.16 (isomer B).

Methyl(2S)-3-(4-{[(5S)-5-[(4-amino-2-oxo-1,2-dihydropyrimidin-1-yl)methyl]-2-oxo-1,4,2λ$^5$-dioxaphosphinan-2-yl]oxy}phenyl)-2-[(2S)-2-amino-3-methylbutanamido]propanoate (Boc-2f). Yield 65%. Obtained from 200 mg of HPMPC as mixture of diastereoisomers A:B in ratio 4:1 (by $^{31}$P NMR). $^1$H NMR (400 MHz, CD$_3$OD) δ: 7.58 (d, J=7.0 Hz, 1H, CH=CH—N, isomer A), 7.56 (d, J=7.0 Hz, 1H, CH=CH—N, isomer B), 7.29-7.14 (m, 4H, aromatics), 5.88 (d, J=6.9 Hz, 1H, CH=CH—N, isomer B), 5.87 (d, J=7.5 Hz, 1H, CH=CH—N, isomer A), 4.73-3.83 (m, 8H), 3.71 (s, 3H, OCH$_3$), 3.18 (dd, J$_{gem}$=13.9 Hz, J=5.4 Hz, 1H, CH$_a$H$_b$(Tyr)), 3.02 (dd, J$_{gem}$=13.9 Hz, J=8.5 Hz, 1H, CH$_a$H$_b$(Tyr)), 1.96 (m, 1H, CH(CH$_3$)$_2$), 1.47 (s, 9H, C(CH$_3$)$_3$), 0.90 (m, 6H, 2CH$_3$). $^{31}$P NMR (162 MHz, CD$_3$OD): δ 9.90 (isomer A), 8.71 (isomer B).

Methyl(2S)-3-(4-{[(5S)-5-[(4-amino-2-oxo-1,2-dihydropyrimidin-1-yl)methyl]-2-oxo-1,4,2λ$^5$-dioxaphosphinan-2-yl]oxy}phenyl)-2-[(2S)-2-amino-3-methylbutanamido]propanoate (Boc-1f). Yield 63%. Obtained from 100 mg of HPMPA as mixture of diastereoisomers A:B in ratio 16:1 (by $^{31}$P NMR). $^1$H NMR (400 MHz, CD$_3$OD): δ 8.25 (s, 1H, 2-H), 8.17 (s, 1H, 8-H, isomer A), 8.14 (s, 1H, 8-H, isomer B), 7.27-7.09 (m, 4H, aromatics), 4.78-3.83 (m, 9H), 3.71 (s, 3H, OCH$_3$, isomer A), 3.70 (s, 3H, OCH$_3$, isomer B), 3.17 (dd, J$_{gem}$=13.9 Hz, J=5.4 Hz, 1H, CH$_a$H$_b$(Tyr)), 3.02 (dd, J$_{gem}$=14.0, Hz, J=8.6 Hz, 1H, CH$_a$H$_b$(Tyr)), 1.95 (m, 1H, CH(CH$_3$)$_2$), 1.47 (s, 9H, C(CH$_3$)$_3$), 0.90 (m, 6H, 2CH$_3$). $^{31}$P NMR (202.5 MHz, CD$_3$OD) δ: 11.4 (isomer A), 10.06 (isomer B).

Boc-Deprotection. General Procedure. TFA (4 mL) was added to a solution of the Boc-protected derivatives (Boc-1a, e,f and Boc-2a-d,f) dissolved in dry CH$_2$Cl$_2$ (4 mL). After stirring overnight at room temperature, volatiles were removed under vacuum. The residue was purified by silica gel column chromatography for compounds 1a,e,f and 2a-d,f [CH$_2$Cl$_2$:MeOH (10:1.5) with addition of 0.5% TFA]. After removing the solvent, compounds 1a,e,f and 2a-d,f were precipitated with diethyl ether, filtered and dried in vacuum to give TFA salts of final products as white powders.

Transfer of the prodrugs from TFA salt into chloride salts. General Procedure. The TFA salt of compound 1a,e or 2a (0.4 mmol) was dissolved in MeOH (20 mL) at −20° C. with stirring, followed by addition of 0.2 M HCl/MeOH (20 mL) with cooling to −20° C. The volatiles were evaporated under vacuum. The procedure was repeated two times. After the third addition and evaporation of the HCl/MeOH solution, the chloride salts of compounds 1a,e and 2a were dried in vacuum and precipitated with diethyl ether as described above for TFA salts.

Methyl-(2S)-2-amino-3-(4-{[(5S)-5-[(4-amino-2-oxo-2H-pyrimidin-1-yl)-methyl]-2-oxo-1,4,2λ$^5$-dioxaphosphinan-2-yl]oxy}phenyl)propanoate (2a). Yield 58%. Obtained as TFA salt and transferred into chloride salt; mixture of diastereoisomers A:B in ratio 3.8:1 (by $^{31}$P NMR). $^1$H NMR (400 MHz, CD$_3$OD): δ 7.94 (m, 1H, CH=CH—N), 7.38-7.24 (m, 4H, aromatics), 6.10 (d, J=8.0 Hz, 1H, CH=CH—N), 4.68 (ddd, J$_{gem}$=15.2 Hz, $^2$J$_{HP}$=13.8 Hz, J=2.8 Hz, 1H, CH$_{eq}$H$_{ax}$O, isomer A), 4.61-4.52 (m, 2H, CH$_{eq}$H$_{ax}$O, isomer B and CH$_{eq}$H$_{ax}$O), 4.47 (dd, J$_{gem}$=14.8 Hz, $^1$J$_{HP}$=7.6 Hz, 1H, CH$_a$H$_b$P), 4.38-4.35 (m, 1H, CHNH$_2$), 4.32-4.23 (m, 2H, CHO and CH$_a$H$_b$P) 4.20-4.07 (m, 2H, CH$_2$N), 3.86 (s, 3H, OCH$_3$ isomer B), 3.85 (s, 3H, OCH$_3$ isomer A), 3.32-3.28 (m, 1H, CH$_a$H$_b$(Tyr)), 3.24-3.17 (1H, m, CH$_a$H$_b$ (Tyr)). $^{31}$P NMR (162 MHz, CD$_3$OD): δ 10.63 (isomer A), 9.01 (isomer B). HRMS: m/z calcd 439.1387 (M+H)$^+$. found 439.1378. (M+H)$^+$LC-MS: t$_R$ 24.05 min.

Methyl(2R)-2-amino-3-(4-{[(5S)-5-[(4-amino-2-oxo-2H-pyrimidin-1-yl)-methyl]-2-oxo-1,4,2λ$^5$-dioxaphosphinan-2-yl]oxy}phenyl)propanoate (2b). Yield 50%. Obtained as TFA salt and transferred into chloride salt; mixture of diastereoisomers A:B in ratio 2.7:1 (by $^{31}$P NMR). NMR (400 MHz, CD$_3$OD): δ 7.89 (d, J=7.6 Hz, 1H, CH=CH—N, isomer A), 7.86 (d, J=8.4 Hz, 1H, CH=CH—N, isomer B), 7.37-7.23 (m, 4H, aromatics), 6.08 (d, J=7.6 Hz, 1H, CH=CH—N), 4.68 (ddd, J$_{gem}$=14.8 Hz, $^2$J$_{HP}$=12.4 Hz, J=2.4 Hz, 1H, CH$_{eq}$H$_{ax}$O, isomer A), 4.63-4.50 (m, 2H, CH$_{eq}$H$_{ax}$O, isomer B and CH$_{eq}$H$_{ax}$O), 4.47 (dd, J$_{gem}$=15.2 Hz, $^1$J$_{HP}$=8.0 Hz, 1H, CH$_a$H$_b$P), 4.38-4.34 (m, 1H, CHNH$_2$), 4.30-4.24 (m, 2H, CHO and CH$_a$H$_b$P) 4.17-4.05 (m, 2H, CH$_2$N), 3.85 (s, 3H, OCH$_3$, isomer B), 3.84 (s, 3H, OCH$_3$, isomer A), 3.30-3.27 (m, 1H, CH$_a$H$_b$ (Tyr)), 3.23-3.16 (m, 1H, CH$_a$H$_b$ (Tyr)). $^{31}$P NMR (162 MHz, CD$_3$OD): δ 10.59 (isomer A), 9.00 (isomer B). HR-MS: m/z calcd 439.1377 (M+H)$^+$. found 439.1387 (M+H)$^+$. LC-MS: t$_R$ 24.13 min (isomer B), 24.54 min (isomer A).

Propan-2-yl-(2S)-2-amino-3-(4-{[(5S)-5-[(4-amino-2-oxo-2H-pyrimidin-1-yl)-methyl]-2-oxo-1,4,2λ$^5$-dioxaphosphinan-2-yl]oxy}phenyl)propanoate] (2c). Yield 22%. Obtained as TFA salt; mixture of diastereoisomers A:B in ratio 2.6:1 (by $^{31}$P NMR). $^1$H NMR (400 MHz, CD$_3$OD): δ 7.79 (d, J=7.2 Hz, 1H, CH=CH—N, isomer A), 7.76 (d, J=7.6 Hz, 1H, CH=CH—N, isomer B), 7.33-7.18 (m, 4H, aromatics), 6.03-6.00 (m, 1H, CH=CH—N), 5.01-5.06 (m, 1H, OCH(CH$_3$)$_2$), 4.60 (ddd, J$_{gem}$=15.2 Hz, $^2$J$_{HP}$=12.4 Hz, J=2.8 Hz, 1H, CH$_{eq}$H$_{ax}$O isomer A), 4.56-4.39 (m, 2H, CH$_{eq}$H$_{ax}$O, isomer B and CH$_{eq}$H$_{ax}$O), 4.42 (dd, J$_{gem}$=14.4 Hz, $^1$J$_{HP}$=7.2 Hz, 1H, CH$_a$H$_b$P, isomer A), 4.37 (dd, J$_{gem}$=15.6 Hz, $^1$J$_{HP}$=11.2 Hz, 1H, CH$_a$H$_b$P, isomer B) 4.27-4.19 (m, 3H, CHNH$_2$, CHO and CH$_a$H$_b$P), 4.13-3.99 (m, 3H, CH$_a$H$_b$N isomer B, CH$_2$N, isomer A), 3.80 (dd, J$_{gem}$=12.4 Hz, J=7.6 Hz, 1H, CH$_a$H$_b$N, isomer B), 3.24-3.13 (m, 2H, CH$_2$(Tyr)), 1.25-1.23 (m, 3H, CH$_3$), 1.18-1.16 (m, 3H, CH$_3$). $^{31}$P NMR (162 MHz, CD$_3$OD): δ 10.41 (isomer A), 8.81 (isomer B). $^{13}$C NMR (100.6 MHz, CD$_3$OD): δ 168.03 (CO), 161.85 (CO), 161.42 (CO), 150.27 (CH=CH—N), 149.48 (CH=CH—N), 149.34 (CNH$_2$), 149.20 (d, J$_{CP}$=8.2 Hz, aromatic COP), 148.63 (d, J$_{CP}$=7.4 Hz, aromatic COP), 131.85 (aromatic C—CH$_2$), 131.73 (aromatic C—CH$_2$), 130.91 (2CH aromatics), 130.84 (2CH aromatics), 120.75 (d, J$_{CP}$=3.8 Hz, 2CH aromatics), 120.63 (d, J$_{CP}$=3.9 Hz, 2CH aromatics), 93.05 (CH=CH—N), 73.75 (d, J$_{CP}$=5.4 Hz, CHO), 72.98 (d, J$_{CP}$=8.4 Hz, CH$_2$OP), 72.89 (d, J$_{CP}$=4.6 Hz, CHOP), 71.32 (d, J$_{CP}$=6.93 Hz, CH$_2$OP), 70.71 (CH(CH$_3$)$_2$), 62.28 (d, J$_{CP}$=144.12 Hz, CH$_2$P), 62.16 (d, J$_{CP}$=146.43 Hz, CH$_2$P), 53.65 (CHNH$_2$), 48.34 (CH$_2$N, overlap with CD$_3$OD signal), 35.30 (CH$_2$(Tyr)), 20.37 (CH$_3$), 20.34 (CH$_3$). HRMS: m/z calcd 467.1700 (M+H)$^+$. found 467.1698 (M+H)$^+$. LC-MS: t$_R$ 23.61 min (isomer B), 24.05 min (isomer A).

(2R)-2-Amino-3-(4-{[(5S)-5-[(4-amino-2-oxo-2H-pyrimidin-1-yl)-methyl]-2-oxo-1,4,2λ$^5$-dioxaphosphinan-2-yl]oxy}phenyl)-N-tert-butyl propanamide] (2d). Yield 53%. Obtained as TFA salt; mixture of diastereoisomers A:B in ratio 2.3:1 (by $^{31}$P NMR). $^1$H NMR (400 MHz, CD$_3$OD): δ 7.86 (d, J=7.6 Hz, 1H, CH=CH—N, isomer A), 7.84 (d, J=8 Hz, 1H, CH=CH—N, isomer B), 7.32-7.17 (m, 4H, aromatics), 6.04 (d, J=7.6 Hz, 1H, CH=CH—N), 4.62 (ddd, J$_{gem}$=14.8 Hz, $^2$J$_{HP}$=12.4 Hz, J=2.8 Hz, 1H, CH$_{eq}$H$_{ax}$O, isomer A), 4.56 (ddd, J$_{gem}$=14.8 Hz, $^2$J$_{HP}$=12.0 Hz, J=2.8 Hz, 1H, CH$_{eq}$H$_{ax}$O, isomer B), 4.51-4.46 (m, 1H, CH$_{eq}$H$_{ax}$O), 4.41 (dd, J$_{gem}$=14.4 Hz, $^1$J$_{HP}$=7.6 Hz, 1H, CH$_a$H$_b$P, isomer A), 4.35 (dd, J$_{gem}$=15.2 Hz, $^1$J$_{HP}$=11.2, 1H, CH$_a$H$_b$P, isomer B) 4.24-4.16 (m, 2H, CHO and CH$_a$H$_b$P) 4.13-4.01 (m, 2H, CH$_a$H$_b$N, isomer B, CH$_2$N, isomer A), 3.92 (m, 1H, CHNH$_2$), 3.80 (dd, J$_{gem}$=14.8 Hz, J=8.4 Hz, 1H, CH$_a$H$_b$N, isomer B), 3.11-3.00 (m, 2H, CH$_2$(Tyr)), 1.24 (m, 9H, NHC(CH$_3$)$_3$, isomer B), 1.23 (m, 9H, NHC(CH$_3$)$_3$, isomer A). $^{31}$P NMR (161.92 MHz, CD$_3$OD) δ: 10.42 (isomer A), 8.87 (isomer B). HRMS: m/z calcd 480.2006 (M+H)$^+$. found 480.2004 (M+H)$^+$. LC-MS: t$_R$ 20.50 min (isomer B), 20.98 min (isomer A).

Methyl(2S)-2-amino-3-(4-{[(5S)-5-[(6-amino-9H-purin-9-yl)methyl]-2-oxo-1,4,2λ$^5$-dioxaphosphinan-2-yl]oxy}phenyl)propanoate (1a). Yield 74%. Obtained as TFA salt and transferred into chloride salt; mixture of diastereoisomers A:B in ratio 5.4:1 (by $^{31}$P NMR). $^1$H NMR (400 MHz, CD$_3$OD), δ 8.41 (s, 1H, 2-H, isomer A), 8.40 (s, 1H, 2-H, isomer B), 8.34 (s, 1H, 8-H, isomer A), 8.30 (s, 1H, 8-H, isomer B), 7.32 (d, J=8.6 Hz, 2H, aromatics), 7.24 (d, J=8.5 Hz, 2H, aromatics), 4.78 (ddd, $^2$J$_{HP}$=12.1 Hz, J$_{gem}$=12.1 Hz, J=3.0 Hz, 1H, CH$_{eq}$H$_{ax}$O, isomer A), 4.69 (dd, J$_{gem}$=15.0 Hz, J=8.3 Hz, 1H, CH$_a$H$_b$N, isomer A), 4.61-4.34 (m, CH$_{eq}$H$_{ax}$O, isomer B; CH$_a$H$_b$N, isomer B; CH$_a$H$_b$N; CH$_{eq}$H$_{ax}$O; CH$_a$H$_b$P; CHO), 4.24 (dd, J$_{gem}$=14.8 Hz, $^1$J$_{HP}$=4.3 Hz, 1H, CH$_a$H$_b$P, isomer A), 4.12 (dd, J$_{gem}$=15.3 Hz, $^1$J$_{HP}$=1.3 Hz, 1H, CH$_a$H$_b$P, isomer B), 3.86 (s, 3H, OCH$_3$, isomer B), 3.85 (s, 3H, OCH$_3$, isomer A), 3.29 (dd, J$_{gem}$=14.5 Hz, J=6.2 Hz, 1H, CH$_a$H$_b$ (Tyr)), 3.18 (dd, J$_{gem}$=14.5 Hz, J=7.4 Hz, 1H, CH$_a$H$_b$ (Tyr)). $^{31}$P NMR (202.5 MHz, CD$_3$OD): δ 10.51 (isomer A), 8.92 (isomer B). HRMS: m/z calcd 463.1489 (M+H)$^+$. found 463.1499 (M+H)$^+$. LC-MS: t$_R$ 17.58 min (isomer B), 18.47 min (isomer A).

(2S)-2-Amino-3-[4-({5-[(6-amino-9H-purin-9-yl)methyl]-2-oxo-1,4,2λ$^5$-dioxaphosphinan-2-yl}oxy)phenyl]-N-(2-methylpropyl)propanamide (1e). Yield 76%. Obtained as TFA salt and transferred into chloride salt; mixture of diastereoisomers A:B in ratio 3.8:1 (by $^{31}$P NMR).

Diastereoisomer A: $^1$H NMR (400 MHz, CD$_3$OD): δ 8.42 (s, 1H, 2-H), 8.37 (s, 1H, 8-H), 7.32 (J=8.6 Hz, 2H, aromatics), 7.19 (d, J=8.6 Hz, 2H, aromatics), 4.76 (ddd, $^2$J$_{HP}$=12.1 Hz, J$_{gem}$=12.1 Hz, J=2.7 Hz, 1H, CH$_{eq}$H$_{ax}$O), 4.70 (dd, J$_{gem}$=14.9 Hz, J=8.3 Hz, 1H, CH$_a$H$_b$N), 4.60 (dd, J$_{gem}$=14.9 Hz, J=3.5 Hz, 1H, CH$_a$H$_b$N), 4.54 (dd, J$_{gem}$=11.7 Hz, $^2$J$_{HP}$=7.4 Hz, 1H, CH$_{eq}$H$_{ax}$O), 4.49 (dd, J$_{gem}$=15.2 Hz, $^1$J$_{HP}$=7.0 Hz, 1H, CH$_a$H$_b$P), 4.42 (m, 1H, CHO), 4.23 (dd, J$_{gem}$=14.9 Hz, $^1$J$_{HP}$=4.3 Hz, 1H, CH$_a$H$_b$P), 4.04 (t, J=7.4 Hz, 1H, CHNH$_2$), 3.17 (dd, J$_{gem}$=14.1 Hz, J=7.6 Hz, 1H, CH$_a$H$_b$ (Tyr)), 3.07 (dd, J$_{gem}$=14.1 Hz, J=7.6 Hz, 1H, CH$_a$H$_b$ (Tyr)), 3.06 (dd, J$_{gem}$=13.3 Hz, J=7.0 Hz, 1H, CH$_a$H$_b$ (i-Bu)), 2.92 (dd, J$_{gem}$=13.3 Hz, J=7.0 Hz, 1H, CH$_a$H$_b$ (i-Bu)), 1.69 (m, J=6.7 Hz, CH(CH$_3$)$_2$), 0.85 (d, J=6.6 Hz, 3H, CH$_3$), 0.82 (d, J=6.7 Hz, 3H, CH$_3$). $^{31}$P NMR (162 MHz, CD$_3$OD): δ 10.31. HRMS: m/z calcd 504.2119 (M+H)$^+$. found 504.2128 (M+H)$^+$. LC-MS: t$_R$ 17.66 min (isomer B), 18.32 min (isomer A).

Methyl(2S)-3-[4-({(5S)-5-[(4-amino-2-oxo-1,2-dihydropyrimidin-1-yl)methyl]-2-oxo-1,4,2λ$^5$-dioxaphosphinan-2-yl}oxy)phenyl]-2-[(2S)-2-amino-3-ethylbutanamido]propanoate (2f). Yield 50%. Obtained as TFA salt; mixture of diastereoisomers A and B in ratio 5.7:1 (by $^{31}$P NMR).

Diastereoisomer A: $^1$H NMR (400 MHz, CD$_3$OD): δ 7.84 (d, J=7.5 Hz, 1H, 6-H), 7.26 (d, J=8.6 Hz, 2H, aromatics), 7.13 (d, J=8.6 Hz, 2H, aromatics), 6.02 (d, J=7.9 Hz, 1H, 5-H), 4.73 (dd, J=8.7 Hz, 5.9 Hz, 1H, CH (Tyr)), 4.62 (ddd, $^2$J$_{HP}$=13.7 Hz, J$_{gem}$=12.1 Hz, J=2.8 Hz, 1H, CH$_{eq}$H$_{ax}$O), 4.48 (dd, J$_{gem}$=12.1 Hz, $^2$J$_{HP}$=7.5 Hz, 1H, CH$_{eq}$H$_{ax}$O), 4.41 (dd, J$_{gem}$=14.5 Hz, $^1$J$_{HP}$=8.0 Hz, 1H, CH$_a$H$_b$P), 4.22 (dd, J$_{gem}$=14.8 Hz, $^1$J$_{HP}$=3.1 Hz, 1H, CH$_a$H$_b$P), 4.20 (m, 1H, CHO), 4.11 (dd, J$_{gem}$=14.5 Hz, J=3.5 Hz, 1H, CH$_a$H$_b$N), 4.03 (dd, J$_{gem}$=14.5 Hz, J=7.8 Hz, 1H, CH$_a$H$_b$N), 3.68 (s, 3H, OCH$_3$), 3.64 (d, J=5.5 Hz, 1H, CHNH$_2$), 3.19 (dd, J$_{gem}$=14.1 Hz, J=5.9 Hz, 1H, CH$_a$H$_b$ (Tyr)), 3.01 (dd, J$_{gem}$=14.1 Hz, J=5.9 Hz, 1H, CH$_a$H$_b$ (Tyr)), 2.20 (m, 1H, CH(CH$_3$)$_2$), 1.06 (d, J=6.6 Hz, 3H, CH$_3$), 1.01 (d, J=6.7 Hz, 3H, CH$_3$). $^{31}$P NMR (202.5 MHz, CD$_3$OD): δ 11.96.

Diastereoisomer B: $^1$H NMR (400 MHz, CD$_3$OD): δ 7.80 (d, J=7.9 Hz, 1H, 6-H), 7.28 (d, J=8.6 Hz, 2H, aromatics), 7.17 (d, J=8.6 Hz, 2H, aromatics), 6.02 (d, J=7.9 Hz, 1H, 5-H), 4.79-3.80 (m, 8H), 3.70 (s, 3H, OCH$_3$), 3.65 (d, J=5.5 Hz, 1H, CHNH$_2$), 3.19 (m, 1H, CH$_a$H$_b$ (Tyr)), 3.01 (m, 1H, CH$_a$H$_b$ (Tyr)), 2.20 (m, 1H, CH(CH$_3$)$_2$), 1.06 (d, J=6.6 Hz, 3H, CH$_3$), 1.01 (d, J=6.7 Hz, 3H, CH$_3$). $^{31}$P NMR (202.5 MHz, CD$_3$OD): δ 10.29.

HR-MS: m/z calcd 538.2061 (M+H)⁺. found 538.2065 (M+H)⁺. LC-MS: $t_R$ 16.06 min (isomer B), 16.43 min (isomer A).

Methyl(2S)-2-[(2S)-2-amino-3-methylbutanamido]-3-[4-({(5S)-5-[(6-amino-9H-purin-9-yl)methyl]-2-oxo-1,4,2λ⁵-dioxaphosphinan-2-yl}oxy)phenyl]propanoate (1f). Yield 54%. Obtained as TFA salt; mixture of diastereoisomers A:B in ratio 1.05:1 (by ³¹P NMR). ¹H NMR (400 MHz, CD₃OD): δ 8.40, 8.39 (2s, 1H, 2-H isomer A and 2-H isomer B), 8.34, 8.30 (2s, 1H, 8-H isom. A and 8-H isomer B), 7.32-7.30 (m, 2H, aromatics), 7.18-7.15 (m, 2H, aromatics), 4.78-4.09 (m, 8H), 3.74, 3.72 (2s, 3H, OCH₃ isomer A and OCH₃ isomer B), 3.69, 3.67 (2d, 1H, CHNH₂ isomer A and CHNH₂ isomer B), 3.26-3.21 (m, 1H, $CH_aH_b$ (Tyr)), 3.09-3.02 (m, 1H, $CH_aH_b$ (Tyr)), 2.29-2.20 (m, 1H, CH(CH₃)₂), 1.06-1.04 (m, 3H, CH₃), 1.06-1.04 (m, 3H, CH₃). ³¹P NMR (202.5 MHz, CD₃OD): δ 10.28 (isomer A), 8.72 (isomer B). HR-MS: m/z calcd 562.2174 (M+H)⁺. found 562.218 (M+H)⁺. LC-MS: $t_R$ 18.99 min (isomer B), 20.35 min (isomer A).

General Method for Isomerization

To a solution of the N-Boc-protected compound (Boc-1e or 2c) (0.2 mmol) and the appropriate N-Boc-protected amino acid (3c,e) (0.02 mmol) in absolute DMF (5 mL) were added molecular sieves (0.4 nm). After 30 min, cesium carbonate (0.4 mmol, 130 mg) was added to the mixture under a nitrogen atmosphere and the reaction mixture was stirred 1-3 days at room temperature, until ³¹P NMR showed a ratio of diastereoisomers A:B~1:9. Molecular sieves and cesium carbonate were removed by filtration and DMF was evaporated under vacuum. The residue was purified by silica gel column chromatography [CH₂Cl₂, CH₂Cl₂:acetone (2:1), and CH₂Cl₂:acetone:CH₃OH (6:3:1)] or deprotected without isolation using TFA/CH₂Cl₂ and purified as described in the general method for Boc-deprotection.

Propan-2-yl-(2S)-3-(4-{[(5S)-5-[(4-amino-2-oxo-2H-pyrimidin-1-yl)methyl]-2-oxo-1,4,2λ⁵-dioxaphosphinan-2-yl]oxy}phenyl)-2-{[(tert-butoxy)carbonyl]amino}propanoate (Boc-2c, enriched by isomer B).

Obtained as a mixture of diastereoisomers A:B in ratio 1:7.8 by ³¹P NMR. ³¹P-NMR (202.5 MHz, CD₃OD) δ: 10.10 (isomer A), 8.76 (isomer B).

Methyl 2-[(2S)-2-amino-3-methylbutanamido]-3-(4-{[(5S)-5-[(6-amino-9H-purin-9-yl)methyl]-2-oxo-1,4,2λ⁵-dioxaphosphinan-2-yl]oxy}phenyl)propanoate. (Boc-1e, enriched by isomer B). Yield 75%. Mixture of diastereoisomers A:B in ratio 1:9.3 (by ³¹P NMR). ³¹P NMR (202.40 MHz, CD₃OD): δ 9.77 (isomer A), 8.50 (isomer B).

Propan-2-yl-(2S)-2-amino-3-(4-{[(5S)-5-[(4-amino-2-oxo-2H-pyrimidin-1-yl)-methyl]-2-oxo-1,4,2λ⁵-dioxaphosphinan-2-yl]oxy}phenyl)propanoate] (2c, enriched by isomer B). Yield 27%. Obtained as TFA salt, mixture of two diastereoisomers A:B in ratio 1:11.5 (by ³¹P NMR).

Diastereoisomer B: ¹HNMR (400 MHz, CD₃OD) δ: 7.84 (d, J=7.2 Hz, 1H, CH=CH—N), 7.33-7.18 (m, 4H, aromatics), 6.05 (d, J=8.0 Hz, 1H, CH=CH—N), 5.00-5.06 (m, 1H, CH(CH₃)₂), 4.57-4.44 (m, 1H, CH₂O), 4.35 (dd, $J_{gem}$=15.2 Hz, $^1J_{HP}$=10.8 Hz, 1H, $CH_aH_b$P), 4.25-4.19 (m, 2H, CHNH₂ and $CH_aH_b$N), 4.16-4.05 (m, 2H, CHO and $CH_aH_b$P), 3.80 (dd, $J_{gem}$=14.4 Hz, J=8.0 Hz, 1H, $CH_aH_b$N), 3.24-3.14 (m, 2H, CH₂ (Tyr)), 1.23 (d, J=6.4 Hz, 3H, CH₃), 1.17 (d, J=6.4 Hz, 3H, CH₃). ³¹P-NMR (162 MHz, CD₃OD) δ: 10.40 (isomer A), 8.86 (isomer B). ¹³C NMR (100.6 MHz, CD₃OD) δ: 168.03 (CO), 160.46 (CO), 150.29 (CH=CH—N), 149.14, (d, $^2J_{CP}$=7.7 Hz, aromatic COP), 147.98 (CNH₂), 131.77 (C—CH₂), 130.92 (2CH aromatics), 120.62 (d, $_3J_{CP}$=4.6 Hz, 2CH aromatics), 92.93 (CH=CH—N), 73.58 (d, $^3J_{CP}$=5.4 Hz, CHO), 72.89 (d, $^2J_{CP}$=8.5 Hz, CH₂OP), 70.67 (CH(CH₃)₂), 61.74 (d, $^1J_{CP}$=143.3 Hz, CH₂P), 53.68 (CHNH₂), 48.14 (CH₂N, overlap with CD₃OD signal), 35.31 (CH₂(Tyr)), 20.37 (CH₃), 20.34 (CH₃). LC-MS: $t_R$ 23.58 min (isomer B), 24.05 (isomer A).

(2S)-2-amino-3-[4-({5-[(6-amino-9H-purin-9-yl)methyl]-2-oxo-1,4,2λ⁵-dioxaphosphinan-2-yl}oxy)phenyl]-N-(2-methylpropyl)propanamide (1e, enriched by isomer B). Yield 73%. Obtained as TFA salt and transferred into chloride salt; mixture of diastereoisomers A:B in ratio 1:9 (by ³¹P NMR).

Diastereoisomer B: ¹H NMR (400 MHz, CD₃OD): δ 8.34 (s, 1H, 2-H), 8.23 (s, 1H, 8-H), 7.32 (J=8.8 Hz, 2H, aromatics), 7.21 (d, J=8.8 Hz, 2H, aromatics), 4.63 (ddd, $^2J_{HP}$=17.6 Hz, $J_{gem}$=11.7 Hz, J=2.0 Hz, 1H, $CH_{eq}H_{ax}$O), 4.52 (dd, $J_{gem}$=14.3 Hz, J=3.2 Hz, 1H, $CH_aH_b$N), 4.48 (ddd, $^2J_{HP}$=11.3 Hz, $J_{gem}$=11.3 Hz, J=0.9 Hz, 1H, $CH_{eq}H_{ax}$O), 4.41 (dd, $J_{gem}$=14.7 Hz, J=7.4 Hz, 1H, $CH_aH_b$N), 4.38 (m, 1H, $CH_{ax}$CH₂N), 4.35 (dd, $J_{gem}$=15.3 Hz, $^1J_{HP}$=11.2 Hz, 1H, $CH_{eq}$ or $H_{ax}$P), 4.10 (dd, $J_{gem}$=15.3 Hz, $^1J_{HP}$=1.2 Hz, 1H, $CH_{eq}$ or $H_{ax}$O), 4.03 (t, J=7.7 Hz, 1H, CHNH₂), 3.17 (dd, $J_{gem}$=14.1 Hz, J=7.6 Hz, 1H, $CH_aH_b$ (Tyr)), 3.08 (dd, $J_{gem}$=14.1 Hz, J=7.6 Hz, 1H, $CH_aH_b$ (Tyr)), 3.07 (dd, $J_{gem}$=13.2 Hz, J=7.0 Hz, 1H, $CH_aH_b$ (i-Bu)), 2.92 (dd, $J_{gem}$=13.2 Hz, J=7.0 Hz, 1H, $CH_aH_b$ (i-Bu)), 1.69 (m, J=7.1 Hz, CH(CH₃)₂), 0.85 (d, J=6.8 Hz, 3H, CH₃), 0.82 (d, J=6.7 Hz, 3H, CH₃). ¹³C NMR (400 MHz, CD₃OD): δ 19.3 (2CH₃), 28.3 (CH(CH₃)₂), 36.8 (CH₂C₆H₄), 43.2 (CH₂—N), 47.1 (CH₂CH(CH₃)₂), 54.5 (CHNH₂), 62.4 (d, $^1J_{CP}$=144.0 Hz CH₂P), 73.2 (d, $^2J_{CP}$=8.6 Hz, CH₂O), 74.2 (d, $^1J_{CP}$=5.5 Hz, CHO), 118.5 (C-5), 120.8 (d, $^3J_{CP}$=4.6 Hz, 2CH aromatics), 131.2 (2CH aromatics), 132.2 (arom. C), 144.2 (C8-H), 146.8 (C2-H), 149.3 (d, $^2J_P$=6.4 Hz, arom. C), 149.4 (C6), 152.4 (C4), 168.2 (CO). ³¹P NMR (162 MHz, CD₃OD): δ 8.72 (s). LC-MS: $t_R$ 17.55 min (isomer B), 18.26 (isomer A).

General Procedure for PyBOP Coupling

To a suspension of (S)-HPMPC or (S)-HPMPA (0.42 mmol) in dry DMF (5 mL), dry DIEA (10 mmol, 1.8 mL) was added. Phenol (60 mg, 0.63 mmol) and PyBOP (1.05 mmol, 0.546 g) were added. The reaction mixture was stirred under N₂ at 40° C. for 2 h. The reaction was monitored by ³¹P NMR, and additional portions of PyBOP were added as necessary. After reaction completion DMF and DIEA were removed under vacuum. The residue was washed with diethyl ether and purified by silica gel column chromatography [CH₂Cl₂, CH₂Cl₂: Acetone (2:1), and CH₂Cl₂:Acetone:CH₃OH (6:3:1)]. Solvents were removed under vacuum yielding the product as a mixture of (S,S)- and (S,R)-diastereoisomers in a ratio 3:1 for cHPMPC-Ph and 4:1 for cHPMPA-Ph. Yield of 3 83%.

Diastereomeric mixtures of cHPMPC-Ph and cHPMPA-Ph enriched by (S,S)-diastereoisomers were further recrystallized as described below to furnish individual (S,S)-diastereoisomers used for X-ray crystallography and NMR experiments.

General Procedure for Isomerization

To a solution of diastereomeric mixture of cHPMPC-Ph or cHPMPA-Ph enriched by (S,S)-diastereoisomer (0.2 mmol) and PhOH (0.02 mmol) in absolute DMF (5 mL) were added molecular sieves 0.4 nm. After 30 min cesium carbonate (0.4 mmol, 130 mg) was added to the mixture under nitrogen atmosphere and reaction mixture was stirred 1 day at room temperature until ³¹P NMR showed ratio of diastereoisomers A:B-1:9. cHPMPC-Ph reaction mixture was heated additionally at 40° C. for 2 h to reach the ratio of (S,S):(S,R)~1:13. Molecular sieves and cesium carbonate were removed by filtration, DMF was evaporated under vacuum. The residue was purified by silica gel column chromatography [CH₂Cl₂, CH₂Cl₂:acetone (2:1), and CH₂Cl₂:acetone:CH₃OH (6:3:1)].

Solvents were removed under vacuum yielding the product as a mixture of (S,S)- and (S,R)-diastereoisomers in a ratio 1:13 for cHPMPC-Ph and 1:4 for cHPMPA-Ph. Yield of 3 74%.

5-[(6-amino-9H-purin-9-yl)methyl]-2-phenoxy-1,4,2λ$^5$-dioxaphosphinan-2-one (4)

(2R,5S)-diastereoisomer. Was obtained by recrystallization from acetonitrile. $^1$H NMR (600 MHz, CD$_3$OD): δ 8.12 (s, 1H, 2-H), 8.01 (s, 1H, 8-H), δ 7.29-7.26 (m, 2H (meta), aromatics), 7.14-7.11 (m, 1H (para), aromatics), 7.07-7.05 (m, 2H (ortho), aromatics), 4.48 (ddd, J=17.6 Hz, J=11.6 Hz, J=2.0 Hz, 1H, CH$_a$H$_b$O), 4.36-4.20 (m, 5H, CH$_a$H$_b$N, CH$_a$H$_b$O, CH$_a$H$_b$P, CHO), 3.97 (dd, J=15.3 Hz, J=1.4 Hz, 1H, CH$_a$H$_b$P). $^{13}$C NMR (126 MHz, CD$_3$OD): 156.05 (C—NH$_2$), 152.51 (C-2), 149.56 (d, $^2$J$_{CP}$=8.3 Hz, aromatic COP), 149.42 (NCC=CNN) 142.05 (C-8), 129.73 (d, $^4$J$_{CP}$=0.7 Hz, 2CH (meta), aromatics), 125.34 (CH (para), aromatics), 119.90 (d, $^3$J$_{CP}$=4.3 Hz, 2CH (ortho), aromatics), 118.33 (NCC=CNN), 73.90 (d, $^3$J$_{CP}$=5.5 Hz, CHO), 72.96 (d, $^2$J$_{CP}$=9.1 Hz, CH$_2$OP), 62.08 (d, $^1$J$_{CP}$=144.1 Hz), 42.55 (CH$_2$N). $^{31}$P NMR (162 MHz, CD$_3$OD): δ 8.45.

(2S,5S)-diastereoisomer. Was obtained by recrystallization from acetonitrile. $^1$H NMR (600 MHz, CD$_3$OD): δ 8.12 (s, 1H, 2-H), 8.03 (s, 1H, 8-H), δ 7.30-7.27 (m, 2H (meta), aromatics), 7.15-7.12 (m, 1H (para), aromatics), 7.11-7.09 (m, 2H (ortho), aromatics), 4.62 (ddd, J=12.1 Hz, J=2.8 Hz, 1H, CH$_a$H$_b$O), 4.48-4.34 (m, 4H, CH$_a$H$_b$N, CH$_a$H$_b$O, CH$_a$H$_b$P), 4.23 (m, 1H, CHO), 4.07 (dd, J=14.8 Hz, J=4.0 Hz, 1H, CH$_a$H$_b$P). $^{13}$C NMR (126 MHz, CD$_3$OD): δ 156.01 (C—NH$_2$), 152.53 (C-2), 149.51 (d, $^2$J$_{CP}$=8.6 Hz, aromatic COP), 149.41 (NCC=CNN) 141.74 (C-8), 129.70 (2CH (meta), aromatics), 125.48 (CH (para), aromatics), 120.11 (d, $^3$J$_{CP}$=4.0 Hz, 2CH (ortho), aromatics), 118.37 (NCC=CNN), 72.97 (d, $^3$J$_{CP}$=5.3 Hz, CHO), 71.42 (d, $^2$J$_{CP}$=7.4 Hz, CH$_2$OP), 61.47 (d, $^1$J$_{CP}$=145.8 Hz, CH$_2$P), 42.16 (CH$_2$N). $^{31}$P NMR (202 MHz, CD$_3$OD): δ 9.81.

4-amino-1-{[2-oxo-2-phenoxy-1,4,2λ$^5$-dioxaphosphinan-5-yl]methyl}-1,2,3,4-tetrahydropyrimidin-2-one (5)

(2R,5S)-diastereoisomer. Was obtained by recrystallization from MeOH/acetone. $^1$H NMR (400 MHz, CD$_3$OD): δ 7.50 (d, J=7.4 Hz, 1H, CH=CH—N), 7.41-7.37 (m, 2H, 2 arom. CH), 7.26-7.21 (m, 3H, 3 arom. CH), 5.83 (d, J=7.6 Hz, 1H, CH=CH—N), 4.52 (ddd, $^3$J$_{PH}$=16.9 Hz, J$_{gem}$=12.0 Hz, J$_{vic}$=3.0 Hz, 1H, CH$_a$H$_b$O), 4.44 (ddd, J$_{gem}$=12.1 Hz, J$_{vic}$=10.1 Hz, $^3$J$_{PH}$=1.8 Hz, 1H, CH$_a$H$_b$O), 4.32 (dd, J$_{gem}$=14.9 Hz, $^2$J$_{HP}$=10.6 Hz, 1H, CH$_a$H$_b$P), 4.20-4.15 (m, 1H, CHO), 4.07 (dd, J$_{gem}$=14.9 Hz, $^2$J$_{PH}$=1.2 Hz, 1H, CH$_a$H$_b$P), 4.01 (dd, J$_{gem}$=14.5 Hz, J$_{vic}$=3.9 Hz, 1H, CH$_a$H$_b$N), 3.77 (dd, J$_{gem}$=14.3 Hz, J$_{vic}$=6.8 Hz, 1H, CH$_a$H$_b$N). $^{31}$P NMR (162 MHz, CD$_3$OD): δ 8.72. $^{13}$C NMR (126 MHz, CD$_3$OD): δ 166.7 (CNH$_2$), 157.6 (CO), 149.62 (d, J=8.4 Hz, arom. C), 147.0 (C-6), 129.8 (2 arom. CH, m-CH), 125.4 (arom. CH, p-CH), 120.0 (d, J=4.3 Hz, 2 arom. CH, o-CH), 94.1 (C-5), 74.3 (d, $^3$J$_{CP}$=5.5 Hz, CHO), 73.2 (d, $^2$J$_{CP}$=8.6 Hz, CH$_2$OP), 62.1 (d, $^1$J$_{CP}$=144.0 Hz, CH$_2$P), 48.5 (CH$_2$N).

(2S,5S)-diastereoisomer. Was obtained by recrystallization from MeOH/acetone/hexane. $^1$H NMR (400 MHz, CD$_3$OD): δ 7.53 (d, J=7.4 Hz, 1H, H-6), 7.40-7.36 (m, 2H 2 arom. CH), 7.25-7.18 (m, 3H, 3 arom. CH), 5.82 (d, J=7.6 Hz, 1H, H-5), 4.52 (ddd, $^3$J$_{PH}$=12.1 Hz, J$_{gem}$=12.0 Hz, J$_{vic}$=2.7 Hz, 1H, CH$_a$H$_b$O), 4.48-4.42 (m, 1H, CH$_a$H$_b$O), 4.32 (dd, J$_{gem}$=14.4 Hz, $^2$J$_{HP}$=7.4 Hz, 1H, CH$_a$H$_b$P), 4.19-4.15 (m, 1H, CHO), 4.17 (dd, J$_{gem}$=15.0 Hz, $^2$J$_{HP}$=3.0 Hz, 1H, CH$_a$H$_b$P), 4.01 (dd, J$_{gem}$=14.2 Hz, J$_{vic}$=3.3 Hz, 1H, CH$_a$H$_b$N), 3.91 (dd, J$_{gem}$=14.2 Hz, J$_{vic}$=8.0 Hz, 1H, CH$_a$H$_b$N). $^{31}$P NMR (162 MHz, CD$_3$OD): δ 9.88.

Hydrolysis of L-Tyr-NH-i-Bu cHPMPA (1e)

TFA salt of (L)-Tyr-NH-i-Bu cHPMPA (1e) (0.16 mmol, 147 mg, 60% of active compound by UV) was dissolved in 8 mL of NH$_4$OH (14.8 M). The reaction mixture was heated at 38° C. for 1 h (reaction was monitored by LC-MS). Products were separated using HPLC (gradient; buffer A: NH$_4$OAc, pH 5.5, 0% ACN; buffer B: NH$_4$OAc, pH 5.5, 30% ACN). Solvents were removed under reduced pressure and the samples were lyophilized.

4-[(2S)-2-amino-2-[(2-methylpropyl)carbamoyl]ethyl] phenoxy({[(2S)-1-(6-amino-9H-purin-9-yl)-3-hydroxypropan-2-yl]oxy}methyl)phosphinic acid (8). Yield 84 mg (56% of active compound by UV). $^1$H NMR (400 MHz, CD$_3$OD): δ 8.17 (s, 1H, 2-H), 8.14 (s, 1H, 8-H), 7.09 (d, J=8.4 Hz, 2H, aromatics), 7.01 (d, J=8.4 Hz, 2H, aromatics), 4.44 (dd, J$_{gem}$=14.7 Hz, $^3$J=3.9 Hz, 1H, CH$_a$H$_b$N), 4.37 (dd, J$_{gem}$=14.5 Hz, $^3$J=6.8 Hz, 1H, CH$_a$H$_b$N), 3.86-3.62 (m, 5H, CHNH$_2$, CH$_a$H$_b$O, CHO, CH$_a$H$_b$P), 3.51 (dd, J=12.5 Hz, J=4.2 Hz, 1H, CH$_a$H$_b$P), 3.12-2.83 (m, 4H, CH$_2$(Tyr), CH$_2$(i-Bu)), 1.73 (m, J=7.6 Hz, CH(CH$_3$)$_2$), 0.87 (d, J=6.7 Hz, 3H, CH$_3$), 0.85 (d, J=6.0 Hz, 3H, CH$_3$). $^{31}$P NMR (202 MHz, CD$_3$OD): δ 13.52 (s). HR-MS: m/z calcd 522.2224 (M+H)$^+$. found 522.2224 (M+H)$^+$.

cHPMPA (6). Yield 19 mg (84% of active compound by UV). $^1$H NMR (400 MHz, D$_2$O): δ 8.17 (s, 1H, 8-H), 8.14 (s, 1H, 2-H), 4.28-4.01 (m, 5H), 3.79 (dd, $^2$J$_{HP}$=8.4 Hz, J$_{gem}$=14.1 Hz), 3.54 (dd, $^2$J$_{HP}$=2.3 Hz, J$_{gem}$=14.1 Hz). $^{31}$P NMR (202 MHz, D$_2$O): δ 9.23 (s). [Holy A., Rosenberg I.: Collect. Czech. Chem. Commun. 52, 1987, 2792].

Example 3

Transport Studies of Tyr(NH-i-Bu) cHPMPA (1e)

IV Injection. Mice (CFW Swiss-Webster) 4 weeks old and weighing 25 g were injected intravenously with drug sample in solution (0.1 mL, conc. 0.6 mg/mL). Due to the sensitivity of cHPMPA assay and the limited volume of the mouse, one mouse represented one time point in these experiments. Groups of 5 mice within the cohort were sacrificed at 0.25, 0.5, 1, 2, 4 h after injection and blood was withdrawn by cardiac puncture.

Oral Gavage. Mice (CFW Swiss-Webster) 4 weeks old and weighing 25 g were fasted for 18 h with free access to water. Drug sample in solution (0.2 mL, conc. 3 mg/mL) was administered by gavage needle. Groups of 5 mice within the cohort were sacrificed at 1, 2, 3, 4, 8, 12, 16, and 24 h and blood was withdrawn by cardiac puncture. Systemic plasma concentrations of the administered prodrug and metabolites were determined using LC-MS/MS analysis.

LC-MS Analysis. Samples for analysis were prepared on a cation exchange solid-phase cartridge (Varian Bond Elut SCX, 100 mg, 1 mL). A 200 μL aliquot of sample was combined with aliquot of internal standard solution, acidified with TFA and loaded onto the activated SPE cartridge. It was washed with 1 mL of 1% TFA in water, 1 mL of methanol and then eluted with 2.5 mL of 5% NH$_4$OH in methanol. The solvent was evaporated at 40° C. under gentle stream of N$_2$ and the residue was reconstituted in 100 μL of water.

Analysis was performed on C-18 HPLC column (5 μm, 50 mm×4.6 mm) at a flow rate of 0.4 mL/min using pH 5.5 ammonium acetate buffer with a gradient from 0 to 30% of acetonitrile. For MS detector, electrospray positive ion mode was used and detector parameters were optimized such that all compounds were analyzed under the same conditions.

Stock solutions of prodrug 1e, its metabolites cHPMPA 6 and acyclic analog 8, as well as internal standard were prepared by dissolving the accurately weighed compounds in water. The standard solutions were then serially diluted to prepare calibration and QC samples. Calibration curves were constructed by plotting the ratio of compound's response to the response of IS versus concentration of the calibration standards. The detection of prodrug 1e was performed by indirect method based on molecular peak of HPMPA dimethyl ester produced as the result of treatment of compound 1e with methanolic ammonia.

REFERENCES

The following publications are incorporated by reference herein in their entirety.

1. Clercq, E. D.; Holy, A.; Rosenberg, I.; Sakuma, T.; Balzarini, J.; Maudgal, P. C. A novel selective broad-spectrum anti-DNA virus agent. *Nature* 1986, 323, 464-467.
2. Clercq, E. D.; Sakuma, T.; Baba, M.; Pauwels, R.; Balzarini, J.; Rosenberg, I.; Holý, A. Antiviral activity of phosphonylmethoxyalkyl derivatives of purine and pyrimidines. *Antiviral Research* 1987, 8, 261-272.
3. Cundy, K. C.; Bidgood, A. M.; Lynch, G.; Shaw, J. P.; Griffin, L.; Lee, W. A. Pharmacokinetics, bioavailability, metabolism, and tissue distribution of cidofovir (HPMPC) and cyclic HPMPC in rats. *Drug Metabolism and Disposition* 1996, 24, 745-752.
4. Bijsterbosch M K, S. L., van Berkel T J. Disposition of the acyclic nucleoside phosphonate (S)-9-(3-hydroxy-2-phosphonylmethoxypropyl)adenine. *Antimicrob Agents Chemother.* 1998 1998, 42, 1146-50.
5. Cundy K C, L. Z., Hitchcock M J, Lee W A. Pharmacokinetics of cidofovir in monkeys. Evidence for a prolonged elimination phase representing phosphorylated drug. *Drug Metab Dispos.* 1996, 24, 738-44.
6. Bijsterbosch, M. K.; Smeijsters, L. J. J. W.; van Berkel, T. J. C. Disposition of the Acyclic Nucleoside Phosphonate (S)-9(3-Hydroxy-2-Phosphonylmethoxypropyl)Adenine. *Antimicrob. Agents Chemother.* 1998, 42, 1146-1150.
7. Peterson, L. W.; McKenna, C. E. Prodrug approaches to improving the oral absorption of antiviral nucleotide analogues. *Expert Opinion on Drug Delivery* 2009, 6, 405-420.
8. Eriksson, U.; Peterson, L. W.; Kashemirov, B. A.; Hilfinger, J. M.; Drach, J. C.; Borysko, K. Z.; Breitenbach, J. M.; Kim, J. S.; Mitchell, S.; Kijek, P.; McKenna, C. E. Serine Peptide Phosphoester Prodrugs of Cyclic Cidofovir: Synthesis, Transport, and Antiviral Activity. *Molecular Pharmaceutics* 2008, 5, 598-609.
9. Kikuchi, C.; Nagaso, H.; Hiranuma, T.; Koyama, M. Tetrahydrobenzindoles: Selective Antagonists of the 5-HT7 Receptor. *Journal of Medicinal Chemistry* 1999, 42, 533-535.
10. Grimm, J. B.; Wilson, K. J.; Witter, D. J. Suppression of racemization in the carbonylation of amino acid-derived aryl triflates. *Tetrahedron Letters* 2007, 48, 4509-4513.
11. Miyazawa T., H. S., Tsuboi Y., Yamada T., Kuwata S. Studies of unusual amino acids and their peptides. XVII. The synthesis of peptides containing N-carboxymethyl amino acids. II. *Bull. Chem. Soc. Jpn.* 1985, 58, 1976-82.
12. Cornish, J.; Callon, K. E.; Lin, C. Q. X.; Xiao, C. L.; Mulvey, T. B.; Cooper, G. J. S.; Reid, I. R. Trifluoroacetate, a contaminant in purified proteins, inhibits proliferation of osteoblasts and chondrocytes. *Am J Physiol Endocrinol Metab* 1999, 277, E779-783.
13. De Clercq E, Neyts, Therapeutic potential of nucleoside/nucleotide analogues against poxvirus infections, J Rev Med Virol. 2004 September-October; 14(5):289-300.
14. Turk, S. R.; Shipman, C., Jr.; Nassiri, R.; Genzlinger, G.; Krawczyk, S. H.; Townsend, L. B.; Drach, J. C. Pyrrolo[2,3-d]pyrimidine nucleosides as inhibitors of human cytomegalovirus. *Antimicrob. Agents Chemother.* 1987, 31, 544-550.
15. Prichard, M. N.; Turk, S. R.; Coleman, L. A.; Engelhardt, S. L.; Shipman, C., Jr.; Drach, J. C. A microtiter virus yield reduction assay for the evaluation of antiviral compounds against human cytomegalovirus and herpes simplex virus. *J. Virol. Methods* 1990, 28, 101-106.
16. Kern, E. R.; Hartline, C.; Harden, E.; Keith, K.; Rodriguez, N.; Beadle, J. R.; Hostetler, K. Y. Enhanced inhibition of orthopoxvirus replication in vitro by alkoxyalkyl esters of cidofovir and cyclic cidofovir. *Antimicrob. Agents Chemother.* 2002, 46, 991-995.
17. Goldstein, A. Biostatistics, an introductory text; Macmillan: New York, 1964, 272 pp.

Although the present invention has been described in connection with the preferred embodiments, it is to be understood that modifications and variations may be utilized without departing from the principles and scope of the invention, as those skilled in the art will readily understand.

What is claimed is:
1. A compound of the formula

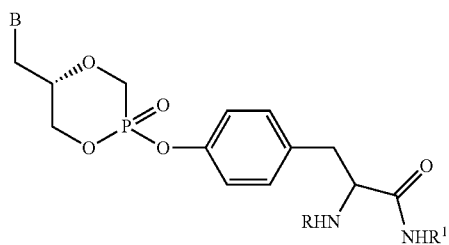

or a salt thereof, wherein:
B is a purine or pyrimidine base;
R is H, an amino acid residue or a derivative thereof, or a $C_1$-$C_4$ alkyl, substituted alkyl, cycloalkyl, or substituted cycloalkyl group; and
$R^1$ is H or a $C_1$-$C_4$ alkyl, substituted alkyl, cycloalkyl, or substituted cycloalkyl group.

2. The compound of claim 1, wherein B is selected from the group consisting of adenine and cytosine.

3. The compound of claim 1, wherein R is H or a valine, alanine, leucine, or isoleucine residue.

4. The compound of claim 1, wherein $R^1$ is H or methyl, ethyl, isobutyl, isopropyl, n-propyl, n-butyl, sec-butyl, or tert-butyl.

5. The compound of claim 1, wherein B is adenine or cytosine base, R is H and $R^1$ is H, methyl or isobutyl.

6. A Boc-protected compound of claim 1.

7. A pharmaceutical composition comprising a compound of claim 1 and a pharmaceutically acceptable carrier.

8. A method of inhibiting viral replication in a DNA virus-infected cell, comprising exposing the cell to a compound of claim 1, wherein the DNA virus is a poxvirus or a herpesvirus.

9. A method of treating a DNA virus infection in an individual, comprising administering to the individual a therapeutically effective amount of a compound of claim 1, wherein the DNA virus is a poxvirus or a herpesvirus.

10. The method of claim 8, wherein the DNA virus is vaccinia virus.

11. The method of claim 8, wherein the DNA virus is cowpox virus.

12. The method of claim 8, wherein the DNA virus is herpes simplex virus.

13. The method of claim 8, wherein the DNA virus is cytomegalovirus.

14. The method of claim 9, wherein the DNA virus is vaccinia virus.

15. The method of claim 9, wherein the DNA virus is cowpox virus.

16. The method of claim 9, wherein the DNA virus is herpes simplex virus.

17. The method of claim 9, wherein the DNA virus is cytomegalovirus.

\* \* \* \* \*